US010488362B2

(12) United States Patent
Laurenson

(10) Patent No.: US 10,488,362 B2
(45) Date of Patent: Nov. 26, 2019

(54) PAPER SUBSTRATE DIAGNOSTIC APPARATUS AND RELATED METHODS AND SYSTEMS

(71) Applicant: Abbott Laboratories, Abbott Park, IL (US)

(72) Inventor: Sophie Laurenson, Basel (CH)

(73) Assignee: ABBOTT LABORATORIES, Abbott Park, IL (US)

( * ) Notice: Subject to any disclaimer, the term of this patent is extended or adjusted under 35 U.S.C. 154(b) by 86 days.

(21) Appl. No.: 15/651,802

(22) Filed: Jul. 17, 2017

(65) Prior Publication Data

US 2017/0315078 A1 Nov. 2, 2017

Related U.S. Application Data

(63) Continuation of application No. 14/920,222, filed on Oct. 22, 2015, now Pat. No. 9,739,747.

(Continued)

(51) Int. Cl.
*B01L 3/00* (2006.01)
*G01N 1/00* (2006.01)
(Continued)

(52) U.S. Cl.
CPC ........... *G01N 27/3275* (2013.01); *B05D 5/00* (2013.01); *B05D 7/58* (2013.01); *G01N 27/327* (2013.01);
(Continued)

(58) Field of Classification Search
CPC .. B01L 3/00; B01L 2300/126; B01L 2300/16; B01L 2300/161; B01L 2300/163;
(Continued)

(56) References Cited

U.S. PATENT DOCUMENTS

| 5,611,339 A | 3/1997 | Okabe et al. |
| 5,736,188 A | 4/1998 | Alcock et al. |

(Continued)

FOREIGN PATENT DOCUMENTS

| AU | 2014100086 | 2/2014 |
| CN | 1922478 | 2/2007 |

(Continued)

OTHER PUBLICATIONS

International Searching Authority, "International Search Report and Written Opinion," issued in connection with International patent application No. PCT/US2015/056468, dated Jan. 14, 2016, 15 pages.

(Continued)

*Primary Examiner* — Brian J. Sines
(74) *Attorney, Agent, or Firm* — Hanley, Flight & Zimmerman, LLC

(57) ABSTRACT

Example paper substrate diagnostic apparatus and related methods and systems are disclosed herein. An example apparatus includes a hydrophobic substrate having a first end and a second end opposite the first end. The apparatus includes a detection zone on a first surface of the substrate, the detection zone defining an area to sense an analyte in a sample, the detection zone comprising a first electrode and a second electrode disposed on the first surface of the substrate and a layer of hydrophilic ink disposed on the two electrodes and an area between the first and second electrodes. The apparatus also includes a channel comprising hydrophilic ink disposed on the first surface of the substrate, the channel having an inlet section adjacent the first end of the substrate, a middle section, and an outlet section in contact with the layer of hydrophilic ink. The channel is to transfer a fluid sample from the inlet section to the layer of hydrophilic ink.

19 Claims, 12 Drawing Sheets

Related U.S. Application Data

(60) Provisional application No. 62/068,424, filed on Oct. 24, 2014.

(51) Int. Cl.

| | | |
|---|---|---|
| *G01N 1/10* | (2006.01) | |
| *G01N 35/00* | (2006.01) | |
| *G01N 33/48* | (2006.01) | |
| *B65C 11/02* | (2006.01) | |
| *B05D 5/00* | (2006.01) | |
| *G01N 27/327* | (2006.01) | |
| *B05D 7/00* | (2006.01) | |

(52) U.S. Cl.
CPC ... *B01L 3/502707* (2013.01); *B01L 2200/141* (2013.01); *B01L 2200/142* (2013.01); *B01L 2300/022* (2013.01); *B01L 2300/023* (2013.01); *B01L 2300/024* (2013.01); *B01L 2300/0645* (2013.01); *B01L 2300/089* (2013.01); *B01L 2300/126* (2013.01); *B01L 2300/161* (2013.01)

(58) Field of Classification Search
CPC ......... B01L 2300/06; B01L 2300/0627; B01L 2300/0636; B01L 2300/0645; B01L 3/502707; G01N 1/00; G01N 1/10; G01N 35/00; G01N 33/48; G01N 27/3275; G01N 27/3276; G01N 27/3277; G01N 27/327; B65C 11/02; C04B 33/32; C04B 33/36; C04B 35/64; B28B 1/00; B28B 3/00; B28B 5/00; B05D 5/00; B05D 7/58
USPC ... 422/502, 503, 504, 68.1, 82.01, 420, 421, 422/425, 426; 436/43, 63, 174, 180; 264/129, 132, 619; 156/384, 387
See application file for complete search history.

(56) References Cited

U.S. PATENT DOCUMENTS

| | | | |
|---|---|---|---|
| 2008/0217407 A1 | 9/2008 | Ackermann et al. | |
| 2011/0105360 A1* | 5/2011 | Derda | B01J 19/0046 506/10 |
| 2013/0069087 A1* | 3/2013 | Onodera | H05K 3/1208 257/88 |
| 2014/0094391 A1 | 4/2014 | McDevitt et al. | |
| 2015/0367340 A1* | 12/2015 | Beachner | B01L 3/502707 422/430 |
| 2015/0367341 A1* | 12/2015 | Zhou | B01L 3/5023 422/430 |
| 2015/0367342 A1* | 12/2015 | Zhou | B01L 3/5023 156/390 |
| 2015/0367615 A1* | 12/2015 | Zhou | B23B 37/0046 156/583.1 |
| 2017/0181278 A1* | 6/2017 | Lessing | D21H 27/00 |

FOREIGN PATENT DOCUMENTS

| | | |
|---|---|---|
| CN | 102286226 | 12/2011 |
| CN | 103022003 | 4/2013 |
| JP | 2007256237 | 10/2007 |

OTHER PUBLICATIONS

International Searching Authority, "International Preliminary Report on Patentability," issued in connection with International patent application No. PCT/US2015/056468, dated May 4, 2017, 9 pages.
Dungchai et al., "Electrochemical Detection for Paper-Based Microfluidics," Analytical Chemistry, vol. 81, No. 14, Jul. 15, 2009, 6 pages.
Jenkins et al., "Printed electronics intergrated with paper-based microfluidics: new methodologies for next-generation healthcare," Microfluidics and Nanofluidics, vol. 19, No. 2, Oct. 9, 2014, 12 pages.
Liana et al., "Recent Advances in Paper-Based Sensors," Sensors, vol. 12, No. 24, Aug. 24, 2012, 22 pages.
Songjaroen et al., "Novel, simple and low-cost alternative method for fabrication of paper-based microfluidics by wax dipping," Talanta, vol. 85 No. 5, Aug. 10, 2011, 8 pages.
United States Patent and Trademark Office, "Restriction and/or Election Requirement," issued in connection with U.S. Appl. No. 14/920,222, dated Apr. 1, 2016, 5 pages.
United States Patent and Trademark Office, "Non-Final Office Action," issued in connection with U.S. Appl. No. 14/920,222, dated Sep. 21, 2016, 10 pages.
United States Patent and Trademark Office, "Notice of Allowance," issued in connection with U.S. Appl. No. 14/920,222, dated Apr. 20, 2017, 8 pages.
National Intellectual Property Administration, P. R. China, "First Office Action", dated Oct. 31, 2018 in connection with Chinese Patent Application No. 201580070837.6, 24 pages.
National Intellectual Property Administration, P. R. China, "Second Office Action", dated Jun. 18, 2019 in connection with Chinese Patent Application No. 201580070837.6, 20 pages.

* cited by examiner

PAPER SUBSTRATE DIAGNOSTIC APPARATUS AND RELATED METHODS AND SYSTEMS

RELATED APPLICATION

This patent arises from a continuation of U.S. application Ser. No. 14/920,222, titled "PAPER SUBSTRATE DIAGNOSTIC APPARATUS AND RELATED METHODS AND SYSTEMS," filed Oct. 22, 2015, which claims the benefit under 35 U.S.C. § 119(e) to U.S. Provisional Application No. 62/068,424, titled "PAPER SUBSTRATE DIAGNOSTIC APPARATUS AND RELATED METHODS AND SYSTEMS," and filed Oct. 24, 2014. U.S. application Ser. No. 14/920,222 and U.S. Provisional Application No. 62/068,424 are is incorporated herein by this reference in their entireties.

FIELD OF THE DISCLOSURE

The present disclosure relates generally to diagnostic apparatus and, more particularly, to paper substrate diagnostic apparatus and related methods and systems.

BACKGROUND

Immunoassays, clinical chemistry assays and/or other medical diagnostic tests are typically performed by automated diagnostic analyzers that test for the presence, absence and/or concentration of a target analyte in a given sample. These automated diagnostic analyzers employ multiple carousels and multiple pipetting mechanisms to automatically aspirate fluid from and dispense fluid to different areas in the analyzer to perform the diagnostic analysis procedures. However, due to the cost, the size, and the complexity of these automated diagnostic analyzers, the analyzers are typically found in laboratories, where large quantities of samples are sent to the laboratory for testing. Therefore, testing a sample with an automated diagnostic analyzer generally takes a greater amount of time before receiving results.

Point-of-care (POC) testing, on the other hand, involves the use of relatively smaller and simpler medical devices that can perform the diagnostic tests at the bedside and/or in an emergency room setting. Some devices used for POC testing utilize small microfluidic chips that include a microfluidic channel and a sensor. A fluid sample can be inserted into the microfluidic channel and transferred to the sensor. The device is then inserted into a reader that communicates with the sensor and determines the results of the test. Known POC devices, however, are generally expensive to manufacture and have poor assay performance.

BRIEF DESCRIPTION OF THE DRAWINGS

The figures are not to scale. Instead, to clarify multiple layers and regions, the thickness of the layers may be enlarged in the drawings. Wherever possible, the same reference numbers will be used throughout the drawing(s) and accompanying written description to refer to the same or like parts.

DETAILED DESCRIPTION

Figure 1:
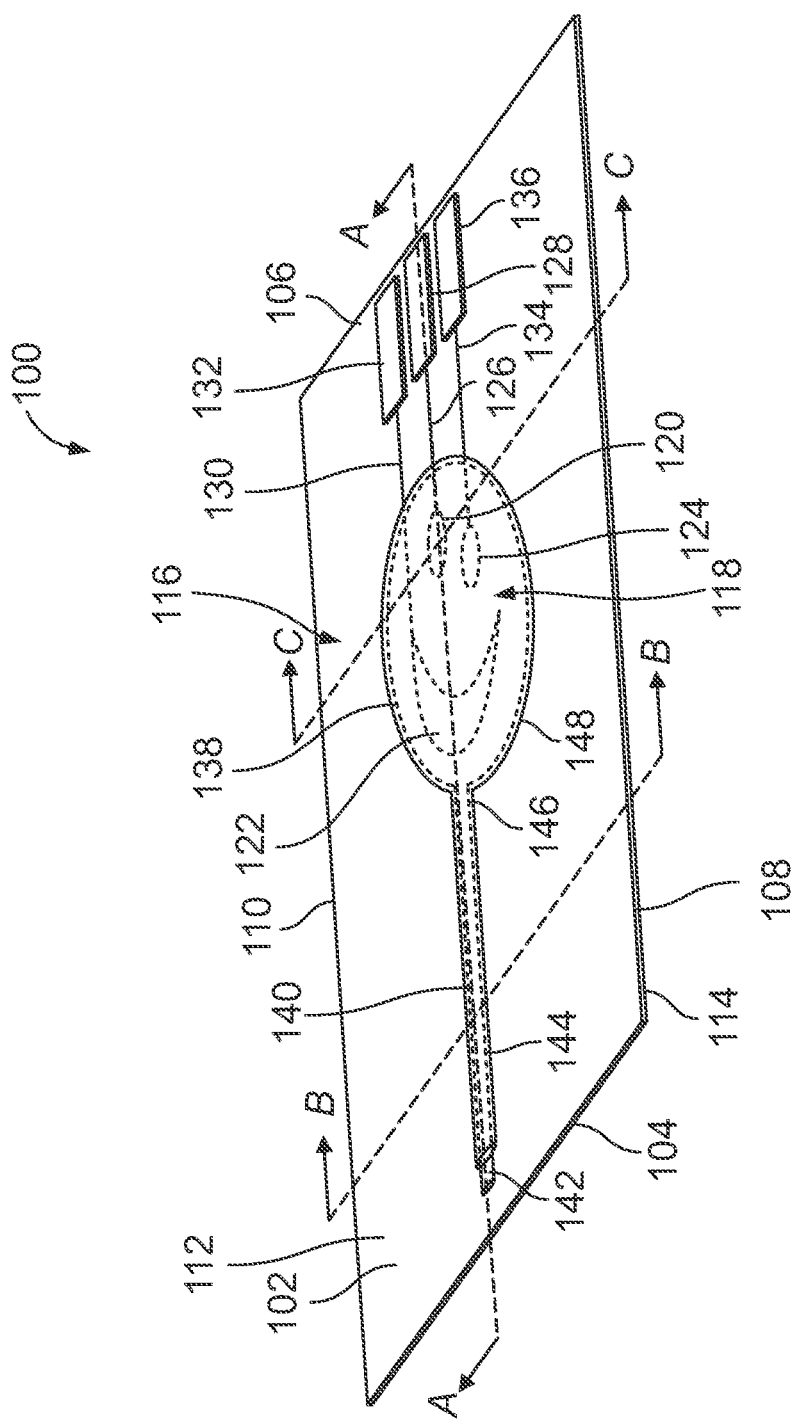
FIG. 1 is a perspective view of an example substrate-based diagnostic apparatus or device constructed in accordance with the teachings of this disclosure.

Immunoassays (IA), clinical chemistry (CC) assays, and/or other medical diagnostic tests (e.g., hematology) are commonly performed by automated diagnostic analyzers in a laboratory. IA and CC tests are used to analyze a specimen or biological sample such as, for example, blood, urine, plasma, etc. for the presence, absence and/or concentration of an item of interest or target (e.g., an analyte). The item of interest or analyte may include, for example, a specific region of DNA, mitochondrial DNA, a specific region of RNA, messenger RNA, transfer RNA, mitochondrial RNA, a fragment, a complement, a peptide, a polypeptide, an enzyme, a prion, a protein, an antibody, an antigen, an allergen, a part of a biological entity such as a cell or a viron, a surface protein, and/or functional equivalent(s) of the above. Specimens such as a patient's body fluids (e.g., serum, whole blood, urine, swabs, plasma, cerebra-spinal fluid, lymph fluids, tissue solids) can be analyzed using a number of different tests to provide information about the patient's health. Generally, analysis of a test sample involves the reaction of test sample with one or more reagents with respect to one or more analytes. The reaction mixtures are analyzed by an apparatus for one or more characteristics such as, for example, the presence, absence and/or concentration of a certain analyte in the test sample. For example, the apparatus disclosed below may be used for testing for analytes related to cancer, thyroid problems, fertility, HIV, or cardiac problems.

Because of the cost, the size, and the complexity of automated diagnostic analyzers, the analyzers are typically used in laboratories to test large batches of samples (e.g., 400 samples). The samples are sent to the laboratory, the tests are performed, and the results are sent back to the clinic or hospital. Therefore, testing via an automated diagnostic analyzer in a laboratory generally requires a longer period of time before receiving the results of the test.

Point-of-care (POC) testing, on the other hand, involves the use of relatively small, simple devices that can be used at the bedside or in an emergency room setting for faster results (e.g., within a few minutes). An at-home pregnancy test is an example of a POC test. IA and CC tests may also be performed via small POC devices. In general, known POC diagnostic devices typically include a small chip or substrate having a detection component for sensing a reaction between the sample and a reagent and a microfluidic component for moving the sample and other liquids throughout the chip. The devices typically include a reagent, which interacts with the sample and a reader for determining the results of the test. The devices move the fluid sample through flow channels and onto the sensor where the reaction may be measured.

Some known devices have a plurality of channels that are machined or patterned into the surface of the chips. However, manufacturing these relatively small, intricate channels results in higher priced manufacturing processes. Some detection devices use magnetic actuation, digital microfluidics (e.g., electrowetting) or acoustic fluidics to move the sample through the device. These techniques likewise result in a more expensive manufacturing process. As a result, known POC diagnostic devices are generally expensive to manufacture and, thus, are expensive to use.

Disclosed herein are example substrate-based (e.g., paper-based) consumable diagnostic devices that are fabricated using less expensive material, cheaper manufacturing processes, and fewer fabrication steps that result in a relatively less expensive diagnostic device. As a result, the disclosed substrate-based diagnostic devices are relatively easier and less expensive to manufacture.

In general, the example substrate-based diagnostic devices disclosed herein include a microfluidic component and a detection component (e.g., a sensor). One example diagnostic device disclosed herein includes a paper substrate having a hydrophobic coating or hydrophobic properties that repel fluid. A sensor, which includes one or more electrodes, is disposed on one surface (e.g., a top surface) of the paper substrate, and a layer of material suspension is disposed on the top surface of the paper substrate and over and around the sensor to define a detection zone. In this example, the material suspension is hydrophilic and includes particles such as, for example, micro-beads or nano-beads that form a porous structure that absorbs or wicks fluids through a network of such particles. To transfer a sample of fluid to the detection zone, the example device also includes a channel of the material suspension that is disposed on the top surface of the paper substrate and leads from one end of the paper substrate to the detection zone. When a sample of fluid is deposited onto the end of the channel, the sample is wicked (e.g., via capillary action) through the channel and into the layer on top of the sensor. In some examples, a reagent is disposed on the top of the sensor (e.g., between an electrode of the sensor and the layer of material suspension). In this manner, the sample can react with the reagent in the detection zone and the sensor can measure the electrical properties generated thereby. Further, a capping layer or fluid impermeable layer is disposed over the channel and the detection zone to form a leak-free pathway between the top surface of the paper substrate (e.g., a bottom boundary) and the capping layer (e.g., an upper boundary). The capping layer reduces evaporation of the fluid sample and also decreases the risk of contamination.

Example systems and methods for constructing or manufacturing the example substrate-based diagnostic device are also disclosed herein. An example system includes a reel-to-reel (e.g., web-fed continuous process) assembly. In this example, a roll of the substrate is unrolled from one reel at one end of the assembly and is rerolled at another end of the assembly. In one or more printing steps, the components (e.g., the sensor, the layer, the channel, the reagent, etc.) of the diagnostic device are printed onto the top surface of the substrate. For example, a conductive ink may be printed onto the substrate to form the electrodes of the sensor. In some examples, the electrodes are printed onto the substrate via inkjet printing, gravure printing, or flexographic printing. The layer and the channel of material suspension (e.g., a hydrophilic ink) may be printed onto the top surface of the substrate via rotary screen printing. The capping layer may also be printed over the layer and the channel via rotary screen printing. In this manner, the microfluidic component and the detection component of the device are able to be printed onto the top of hydrophobic substrate, rather than using complex lithography or machining processes such as that employed by known devices. As a result, the substrate-based diagnostic device is less expensive to manufacture and, thus, is a more cost effective disposable POC device.

Another example diagnostic device disclosed herein utilizes a substrate (e.g., a paper substrate) having hydrophilic qualities. In such an example, the microfluidic component and the detection component are printed into the material of the substrate. A sensor, which may include one or more electrodes, is printed onto the paper substrate and the conductive ink is absorbed into the material of the paper substrate. To form a channel and detection zone, a hydrophobic barrier is printed onto the paper substrate and defines a boundary that prevents the spread of fluid outside of the hydrophobic barrier. In some examples, an additional hydrophilic mesh layer may be printed onto the paper substrate between the hydrophobic barrier. The hydrophilic mesh layer increases the amount of wicking through the material of the paper substrate. In some examples, a hydrophobic substrate is coupled (e.g., laminated, bonded) to the top surface of the paper substrate and forms a capping layer over the channel and the detection zone. The hydrophobic substrate may include sample and/or reagent inlet ports formed in the hydrophobic substrate that allow liquid samples and/or reagents to pass through the hydrophobic substrate and into the material of the paper substrate for testing.

An example apparatus disclosed herein includes a hydrophobic substrate having a first end and a second end opposite the first end. The apparatus includes a detection zone on a first surface of the substrate, the detection zone defining an area to sense an analyte in a sample, the detection zone comprising a first electrode and a second electrode disposed on the first surface of the substrate and a layer of hydrophilic ink disposed on the two electrodes and an area between the first and second electrodes. The apparatus also includes a channel comprising hydrophilic ink disposed on the first surface of the substrate, the channel having an inlet section adjacent the first end of the substrate, a middle section, and an outlet section in contact with the layer of hydrophilic ink. The channel is to transfer a fluid sample from the inlet section to the layer of hydrophilic ink.

In some examples, the apparatus includes a fluid-impermeable layer patterned over the substrate to cover the detection zone, the middle section of the channel, and the outlet section of the channel. In some examples, the fluid-impermeable layer is in contact with the first surface of the substrate proximate the channel and the layer of hydrophilic ink. In some examples, the fluid-impermeable layer comprises nanofiber cellulose (NFC) in a water-based suspension. In some examples, the fluid-impermeable layer is a hydrophobic ink that is to be deposited by at least one of flexographic printing, screen printing, stencil printing, or inkjet printing.

In some examples, the apparatus includes a reagent layer disposed on a top surface of the first electrode, between the first electrode and the layer of hydrophilic ink. In some examples, the first electrode is functionalized with a reagent.

In some examples, the hydrophilic ink comprises microbeads or nano-beads and a binder to adhere the micro-beads or nano-beads to the first surface of the substrate. In some such examples, the binder comprises at least one of polyvinyl chloride (PVC), polyvinylpyrrolidone (PVP), or nanofiber cellulose (NFC).

In some examples, the apparatus includes a first contact disposed on the top surface of the substrate, the first contact is electrically coupled to the first electrode, a second contact disposed on the top surface of the substrate, the second contact is electrically coupled to the second electrode, and a reader. In some such examples, the reader includes a slot to receive at least a portion of the substrate including the first contact and the second contact, electrical connectors to receive signals from the first contact and the second contact and a processor to determine one or more of amperometric, voltammetric, or potentiometric measurements to sense a biomolecular interaction occurring in the detection zone via the first and second electrodes. In some examples, the sensor further comprises a third electrode and the processor is to sense the biomolecular interaction by comparing (1) a difference in the first and second electrodes and (2) a difference in the second and third electrodes. In some examples the detection zone comprises a plurality of additional electrodes, and the processor is to determine a plurality of measurements using the plurality of additional electrodes.

In some examples, the substrate comprises paper. In some examples, the substrate is flexible and printable.

An example method of manufacturing a substrate-based diagnostic device is disclosed herein. The example method includes depositing a sensor on a top surface of the substrate, the substrate having a first end and a second end opposite the first end, depositing a layer of hydrophilic ink over the sensor and depositing a pathway of hydrophilic ink onto the top surface of the substrate. The pathway leads from an area adjacent the first end of the substrate to the layer of hydrophilic ink.

In some examples, the method includes depositing a layer of hydrophobic ink on top of the pathway and the layer of hydrophilic ink. In some examples, the hydrophobic ink comprises nanofiber cellulose (NFC) in a water-based suspension. In some examples, depositing the layer of hydrophobic ink includes printing the hydrophobic ink using at least one of a flexographic printer, a screen printer, a stencil printer, or an inkjet printer.

In some examples, the sensor includes a first electrode and a second electrode, and depositing the sensor includes printing the first electrode and the second electrode onto the top surface of the substrate. In some such examples, the method includes depositing a layer of reagent on the first electrode. In some examples, the layer of reagent is disposed between the first electrode and the layer of hydrophilic ink. In some examples, the first electrode is functionalized with a reagent.

In some examples, depositing the layer of hydrophilic ink and depositing the pathway of hydrophilic ink includes printing the hydrophilic ink using at least one of a flexographic printer, a screen printer, a stencil printer, or an inkjet printer.

Turning now to the figures, FIG. 1 illustrates an example substrate-based diagnostic device 100 used for measuring and/or sensing the presence, absence and/or concentration of an item of interest or analyte in a fluid sample. The example device 100 produces results in a relatively short amount of time, and the device 100 can be manufactured relatively inexpensively. In some examples, either an IA test or a CC test is performed on the device 100, depending on the type of reagent used and the detection method employed. To provide a support surface for the detection component(s) and microfluidic component(s) (disclosed in detail below), the device 100 includes a substrate or backing sheet 102. In the illustrated example, the substrate 102 comprises a strip or a sheet of paper. The example paper substrate 102 is hydrophobic (e.g., fluid impermeable, fluid resistant) and repels fluids or reduces the amount of fluid that is permeable into the paper substrate 102. In some examples, the paper substrate 102 is manufactured from hydrophobic material (e.g., from trees and/or chemicals having hydrophobic properties). In other examples, the paper substrate 102 has a porous structure and is treated with a hydrophobic coating that prevents fluids from permeating into the porous structure of the paper substrate 102.

In the illustrated example, the paper substrate 102 has a first end 104, a second end 106 opposite the first end 104, a first side 108, a second side 110 opposite the first side 108, a top surface 112 and a bottom surface 114 opposite the top surface 112. The top surface 112 defines a support surface for the microfluidic component(s) and detection component(s). In the illustrated example, the paper substrate 102 is substantially rectangular. However, in other examples, the paper substrate 102 may be in another shape such as, for example, a square, a triangle, a circle, an ellipse, an irregular shape, or any other shape capable of supporting the microfluidic and/or detection components disclosed herein.

In an example operation, a fluid sample is pippetted or otherwise deposited at or near the first end 104 of the substrate at or near an opening 142 of a pathway or channel 140. In the illustrated example, the channel 140 is disposed on the top surface 112 of the paper substrate 102. The example channel 140 includes a first end 142 (e.g., a sample deposit area, an inlet), a middle section 144, and a second end 146 (e.g., an outlet). In other examples, there may be more than one channel. The channel 140 is used to transfer the sample to a detection zone 116, which is disclosed in greater detail below. To transfer or move a fluid sample to the detection zone 116, the example channel 140 comprises suspended material, which may be in the form of a network of particles, hydrophilic mesh and/or a hydrophilic ink. The example hydrophilic ink of the channel 140 wicks the fluid sample via capillary action from one end of the channel 140 to the other end of the channel 140. The second end 146 is in contact with a layer 138 of suspended material (e.g., hydrophilic mesh and/or hydrophilic ink) of the detection zone 116. As a result, a fluid that is wicked through the channel 140 from the first end 142 of the channel 140 through the middle section 144, and through the second end 146 is moved into the layer 138 of the detection zone 116, where the sample comes in contact with one or more reagents and electrodes 120, 122, 124, as provided in greater detail below.

The hydrophilic mesh or ink layer 138 enables the sample to move across the substrate 102 in the detection zone 116 to come into contact with a sensor 118, including the electrodes 120, 122, 124, during a reaction. The layer 138 is disposed over the sensor 118 and the area on the top surface 112 surrounding the sensor 118. In the illustrated example, the layer 138 covers the electrodes 120, 122, 124 and the area surrounding the electrodes 120, 122, 124. In some examples, the layer 138 may only cover a portion of the electrodes 120, 122, 124.

The material suspension or hydrophilic ink disposed in the channel 140 and the layer 138 includes a suspension of particles such as, for example, micro-beads (e.g., silica beads of 25-36 micrometers (μm), 10 μm for aqueous solutions) or nano-beads, that create a porous and immobile structure (e.g., a network or matrix of hydrophilic particles). Some of the particles may be hydrophilic and other of the particles may be hydrophobic, and the particles may vary in dimension and size. In some examples, the particles of the material suspension are greater than 20 μm and less than 100 μm in diameter. In other examples, other size diameter particles are utilized. In some examples, the particles are water-based for biological compatibility. The resulting hydrophilic structure absorbs fluids (e.g., via wicking or capillary action). As a result, the layer 138 absorbs the fluid sample such that the sample comes in contact with (e.g., wets) the electrodes 120, 122, 124 of the sensor 118.

In some examples, the hydrophilic ink also includes binders that are mixed with the particles to assist in binding (e.g., adhering) the hydrophilic ink to the paper substrate 102. In some examples, the binders include polyvinyl chloride (PVC), polyvinylpyrrolidone (PVP), and/or nanofiber cellulose (NFC). In other examples, other types of binders may be utilized. The binders and particles may be mixed in varying proportions and, in some examples, may be mixed with additional solvents. The proportions or percentage of binders and particles affect the properties (e.g., wicking rate) of the hydrophilic ink. Thus, the composition of the material suspension or hydrophilic ink of the channel 140 may be varied to control the fluid flow. Other factors also may be used to control the fluid flow include the characteristics of the particles including, for example, the hydrophilicity and/or the dimensions of the particles, the binder type, the percentage composition of material suspension (the ratio of particles to the fluid volume), and/or the channel dimensions including width, length, and/or height.

In some examples, the hydrophilic ink of the channel 140 is the type of hydrophilic ink used in the layer 138. In other examples, the hydrophilic ink of the channel 140 is different than the hydrophilic ink of the layer 138. For example, the hydrophilic ink of the channel 140 may include a different proportion of particles and binders than the hydrophilic ink of the layer 138 (e.g., that result in different wicking rates).

In the illustrated example, the hydrophilic ink of the channel 140 and/or the layer 138 is printed (e.g., patterned) onto the device 100 using a printing process such as, for example, gravure printing, flexographic printing, screen printing, rotary screen printing, and/or inkjet printing. In other examples, other suitable types of printing processes may be used to print the hydrophilic ink onto the paper substrate 102 to form the channel 140 and/or the layer 138. In some examples, the channel 140 and the layer 138 are printed onto the paper substrate 102 during the same printing process. In some examples, the type of printing process is determined based on the desired dimension (e.g., thickness, width and/or length) of the layer 138. For example, in some examples, flexographic printing enables relatively finer resolution of channel structures and is compatible with particles of less than 10 μm. In some examples, screen printing or stencil printing produces larger channel structures and is compatible with a relatively larger range of particle sizes (e.g., depending on the characteristics of the printing mesh utilized).

In the illustrated example, the device 100 includes the detection zone 116 disposed on the top surface 112 of the paper sheet 102. The detection zone 116 defines a location where a reaction occurs (e.g., in order for the fluid sample to be tested via an electronic reader). The detection zone 116 includes the sensor 118 for detecting a reaction between the sample and one or more reagent(s). The detected information is used to determine, for example, the presence, absence and/or concentration of the target analyte in the sample. In the illustrated example, the sensor 118 is an electro-chemical sensor and includes a first electrode 120 (e.g., a working electrode) and a second electrode 122 (e.g., a counter-electrode, a ground electrode) that are disposed on the top surface 112 of the paper substrate 102. Biomolecular interactions occurring on the surface of the electrodes may be measured using electrical and/or electro-chemical methods including amperometric, voltammetric and/or potentiometric techniques. The electrical and/or electro-chemical results that occur across the two electrodes 120, 122 may be correlated to the presence, absence and/or concentration of the target analyte in the sample. In the illustrated example, a third electrode 124 (e.g., a reference electrode) is also disposed on the top surface 112 of the paper substrate 102. In some examples, the first electrode 120 is a working electrode, the second electrode 122 is a ground or counter electrode, and the third electrode 124 is a reference electrode. By measuring the difference between the first and second electrodes 120, 122 (e.g., the working/counter electrode pair) and the second and third electrodes 122, 124 (e.g., the reference/counter electrode pair), a measurement can be made that eliminates noise and/or other interference. In some examples, only two electrodes are implemented such as, for example, a working and a counter (e.g., ground) electrode. In still other examples, multiple electrodes (e.g., four, six, nine, etc.) are used. In such an example, multiple measurements may be made on the same device for detecting multiple analytes.

In the illustrated example, the device 100 employs electrical type sensing via the sensor 118. However, in other examples, other types of sensors may be implemented such as, for example, an optical sensor, a magnetic sensor, or a mechanical sensor.

In some examples, the one or more of the electrodes 120, 122, 124 comprise gold (Au), gold on silver chloride (AgCl), carbon (C), and/or silver/silver chloride (Ag/AgCl). In some examples, one or more of the electrodes 120, 122, 124 are printed onto the top surface 112 of the paper substrate 102 using conductive ink. For example, one or more of the electrodes 120, 122, 124 may be printed onto the device using gravure printing, flexographic printing, screen printing, rotary screen printing, and/or inkjet printing. In other examples, other suitable types of printing processes may be employed to print the conductive ink onto the paper substrate 102.

To enable an electronic reader (disclosed in detail below) to electrically communicate with the electrodes 120, 122, 124, the device 100 includes one or more contacts. In the illustrated example, a first trace 126 (e.g., a wire, a lead, etc.) and a first contact 128 are disposed on the top surface 112 of the of the paper substrate 102. The first trace 126 electrically couples the first electrode 120 to the first contact 128. In the illustrated example, the first contact 128 is located near the second end 106 of the paper sheet 102. However, in other examples, the first contact 128 can be disposed in other locations on the paper sheet 102.

In the illustrated example, a second trace 130 and a second contact 132 are disposed on the top surface 112 of the paper sheet 102 for the second electrode 122, and a third trace 134 and a third contact 136 are disposed on the top surface 112 of the paper sheet 102 for the third electrode 124. In the illustrated example, the three contacts 128, 132, 136 are disposed in a row near the second end 106 of the paper sheet 102. As a result, the second end 106 of the device can be inserted into a reader having pins that engage the contacts 128, 132, 136. In some examples, the traces 126, 130, 134 and the contacts 128, 132, 136 are printed onto the top surface 112 of the paper substrate 102 using printing processes similar to that of the electrodes 120, 122, 124 disclosed above.

In performing IA and CC tests, one or more reagents are commonly used to interact with the sample. In some examples, one or more reagents (illustrated in FIG. 2D) are disposed on top of the first electrode 120 (e.g., the working electrode). As the sample comes in contact with the first electrode 120, the sample interacts with the reagent, and the biomolecular interaction causes a change in volts, amps, and/or resistance that can be measured across the first and second electrodes 120, 122. For example, the sensor 118 may be a nano-wire field effect transistor (FET) sensor. In such an example, the gate of the FET may be functionalized with the reagent, and the electro-chemical reaction between the sample on the gate may be measured. The resulting change in electrical activity can be correlated and/or used to determine the presence, absence and/or concentration of the target analyte in the sample (e.g., by comparing the results to reference data). In other examples, one or more reagents are functionalized directly into the material of the first electrode 120. In other examples, one or more reagents may be disposed (e.g., via printing) onto the top surface 112 of the paper substrate 112 (e.g., under the channel 140 or the layer 138). As the sample is wicked through the channel 140 and/or layer 138, the sample reacts with the one or more reagents.

In some examples, analyte detection may be performed using label-free detection such as, for example, impedance, capacitance, or resistance techniques that recognize the analyte of interest. Additionally or alternatively, a second binding reagent may be employed that recognizes a different region of the analyte of interest. In some examples, the second binding reagent improves specificity of detection, enhances sensitivity of detection, and/or improves a dynamic range of the assay. The second binding reagent may be conjugated to a label including conductive particles (e.g., metal colloids such as gold, silver, copper, platinum, carbon micro-particles, and/or carbon nano-particles and/or conductive polymer particles), quantum dots, latex particles, magnetic particles (e.g., magnetic micro-particles and/or magnetic nano-particles). In some examples, detection relies on the use of redox mediators and an enzyme catalyst that is deposited on the electrode surface (e.g., the surface of the first electrode 120).

In some examples, to protect exposed conductive traces, a dielectric barrier material may be deposited (e.g., via printing) in a specified pattern. In some examples, a dielectric ink is used, and the dielectric ink anchors and seals the hydrophilic ink of the channel 140 and/or the hydrophilic ink of the layer 138 to the substrate 102. In some examples, the dielectric ink defines the reaction volumes exposed to the sensor 118. In other examples, an impermeable membrane or resist layer may be placed in the desired location and sealed by lamination.

To prevent contamination and/or evaporation of the fluid sample as it moves through the channel 140 and the layer 138 and interacts with the reagents in the detection zone 116, the example device 100 includes a capping layer 148, which is disposed over the channel 140 and the layer 138. The capping layer 148 creates a fluid-impermeable (or hydrophobic) surface over the top of the hydrophilic ink of the channel 140 and the layer 138. In the illustrated example, the capping layer 148 is not disposed on top of the first end 142 of the channel 140, so that the fluid sample may be deposited at the first end 142 of the channel 140 onto the hydrophilic ink of the channel 140. In other examples, the entire channel 140 is covered with the capping layer 148 and an opening or hole is defined in the capping layer 148 to allow the fluid sample to come into contact with the hydrophilic ink of the channel 140.

In the illustrated example, the capping layer 148 is in contact with the top surface 112 of the paper substrate 102 on the immediate sides of the channel 140 and the layer 138 of the detection zone 116. As a result, the capping layer 148 forms or defines a sealed (e.g., leak-free) pathway between the capping layer 148 and the top surface 112 of the paper substrate 102. In some examples, the capping layer 148 is an ink that is printed over the channel 140 and detection zone 116. In some examples, the ink includes NFC in a water based suspension. In some examples, the capping layer 148 ink is printed onto the device via flexographic printing, screen printing, stencil printing, and/or inkjet printing. In other examples, other types of printing processes may be utilized. In the illustrated example, the capping layer 148 is not disposed on the remainder of the paper substrate 102 away from the channel 140 and the layer 138. As a result, less material is used to cap or seal the channel 140 and the layer 138. However, in other examples, the capping layer may be printed over the entire paper substrate 102.

In some examples, the composition of the conductive ink(s), the capping layer (e.g., hydrophobic) ink(s), hydrophilic ink(s), and/or dielectric ink(s) may depend on the properties of the substrate 102 and/or the printing processes used. For example, the conductive ink may need to be cured or dried after deposition (e.g., via ultra-violet light, heat, infrared (IR), or air-drying) depending on the ink composition and/or the tolerances of the substrate.

Figure 2A:
FIGS. 2A-2F are cross-sectional views taken along line A-A in FIG. 1 during different stages of formation of the example substrate-based diagnostic device of FIG. 1.

FIGS. 2A-2F are cross-sectional views of the device 100 taken along line A-A in FIG. 1. FIGS. 2A-2F illustrate example steps for fabricating or constructing the device 100. It should be noted, that the figures are not necessarily to scale. In fact, the elements of the figures have been accentuated for illustration purposes. The example paper substrate 102 is illustrated in FIG. 2A. In some examples, the paper substrate 102 is preprocessed as a sheet of hydrophobic paper. For example, the paper substrate 102 may be manufactured from materials and/or chemicals that result in a hydrophobic paper substrate. In other examples, the paper substrate 102 may be a more traditional piece of porous paper that is treated with a hydrophobic coating or layer.

Figure 2B:
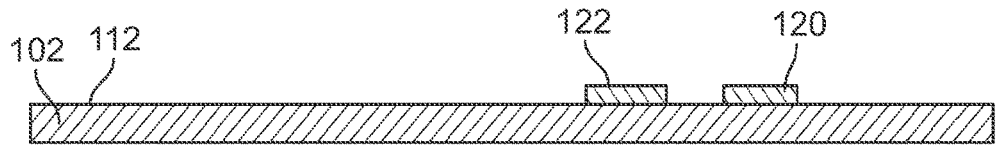

In the illustrated example of FIG. 2B, the first and second electrodes 120, 122 of the sensor 118 (FIG. 1) are disposed on the top surface 112 of the paper substrate 102. In some examples, the first and second electrodes 120, 122 are printed onto the top surface 112 using conductive ink. The conductive ink may be printed onto the top surface 112 via gravure printing, flexographic printing, screen printing, rotary screen printing, inkjet printing, or any other suitable printing process. The third electrode 124 is not shown in this illustration, but it is to be understood that similar printing processes may be used to print the third electrode 124 onto the top surface 112 of the paper substrate.

Figure 2C:
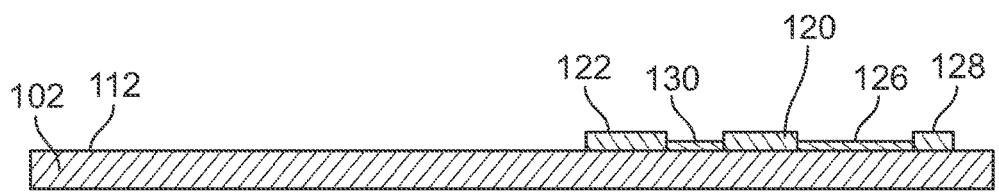

In the illustrated example of FIG. 2C, the first and second traces 126, 130 and the first and second contacts 128, 132 are disposed on the top surface 112 of the paper substrate 102. In some examples, the first and second traces 124, 128 and the first and second contacts 126, 130 are deposited onto the top surface 112 using conductive inks via a printing process such as, for example, gravure printing, flexographic printing, screen printing, rotary screen printing, or inkjet printing. In some examples, the electrodes 120, 122 (and/or 124), the traces 126, 130 (and/or 134), and the contacts 128, 132 (and/or 136) are all printed onto the paper substrate 102 during a single printing process. In other examples, each of the electrodes, traces, and/or contacts may be printed via a separate printing process (e.g., the first electrode 120 is printed via a first rotary screen printer and the second electrode 122 is printed via a second rotary screen printer).

Figure 2D:
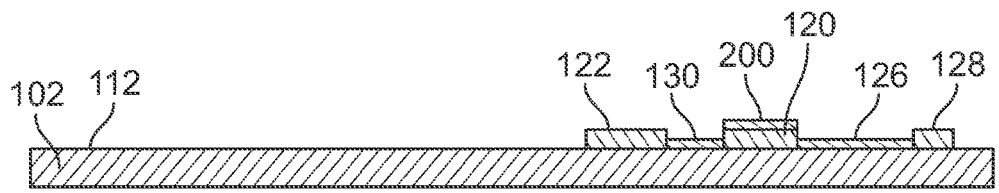

In the illustrated in the example FIG. 2D, one or more reagents 200 are disposed on the top of the first electrode 120. As the fluid sample comes into contact with the first electrode 120, the fluid sample mixes with the reagent 200 and results in the biomolecular interaction. The reagent 200 may be deposited onto the surface (e.g., the top surface and/or the side surface(s)) of the first electrode 120 via a printing process such as, for example, inkjet printing, flexographic printing, gravure printing, screen-printing, or slot die deposition. In other examples, the reagent 200 is embedded in a hydrogel or other polymer and printed as a suspension, which is later cured (e.g., via ultraviolet (UV) light or electropolymerization). In other examples, the reagent 200 is mixed (e.g., functionalized) directly into the material of the first electrode 120. In such an instance, as the fluid sample comes into contact with the first electrode 120, a reaction occurs on the surface of the first electrode 120 that can be measured (e.g., correlated) as the presence, absence and/or concentration of the target analyte.

Figure 2E:
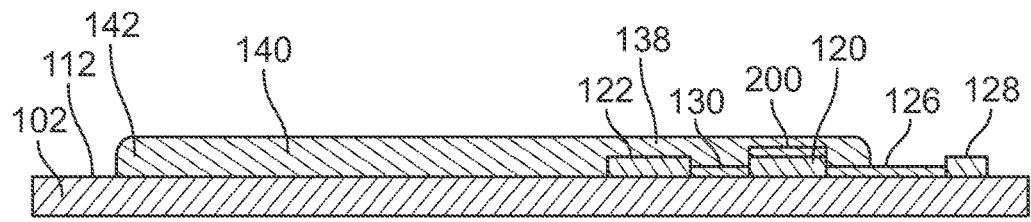

In the illustrated example of FIG. 2E, the layer 138 of hydrophilic ink is deposited onto the top surface 112 of the paper substrate 102 over the first and second electrodes 120, 118, and the channel 140 of hydrophilic ink is deposited onto the top surface 112 of the paper substrate 102. In some examples, the hydrophilic ink of the layer 138 and the hydrophilic ink of the channel 140 are the same ink. In other examples, different ink may be used to affect different flow rates through the channel 140 and the layer 138, as disclosed above. In operation, a sample of fluid may be deposited at the first end 142 of the channel 140, and the hydrophilic ink of the channel 140 wicks (e.g., via capillary action) the fluid sample to the layer 138, which covers the sensor 118 (FIG. 1). As a result, the sample contacts and interacts with the reagent 200, which produces an electrical signal that is detectable by the first electrode 120. The hydrophilic ink of the channel 140 and/or the layer of hydrophilic ink 138 are deposited onto the substrate 102 via one of the processes disclosed above.

Figure 2F:
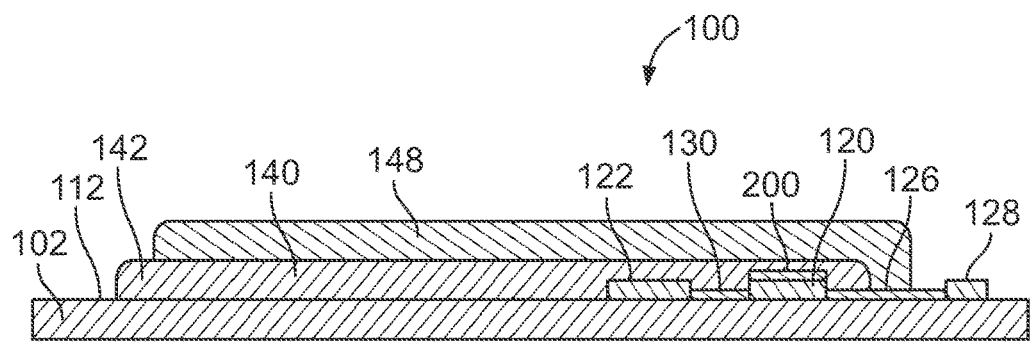

In the illustrated example of FIG. 2F, the capping layer 148 is deposited over the layer 138 and the channel 140. The capping layer 146 is a fluid impermeable layer, which reduces the amount of sample evaporation and the risk of contamination such as, for example, by an operator accidentally touching the hydrophilic ink. In the illustrated example, the first end 142 of the channel 140 is not covered by the capping layer 148, so that the fluid sample can be deposited onto the hydrophilic ink of the channel 140.

Figure 3A:
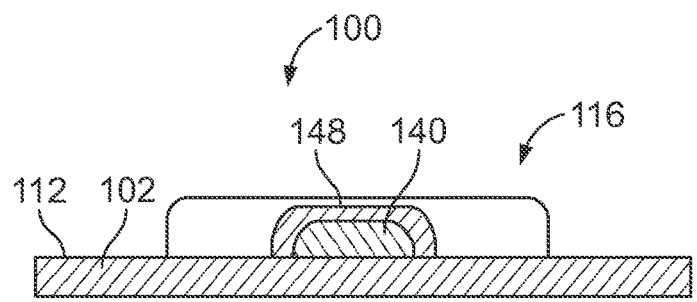
FIG. 3A is cross-sectional view taken along line B-B in FIG. 1 of the example substrate-based diagnostic device of FIG. 1.

FIG. 3A is a cross-sectional view of the example device 100 taken along line B-B of FIG. 1. In the illustrated example, the capping layer 148 covers the top and sides of the channel 140 and, thus, a leak-free pathway is formed or defined by the capping layer 148 (e.g., the upper boundary) and the top surface 112 of the paper substrate 102 (e.g., the lower boundary). The detection zone 116 is shown in distance behind the channel 140.

Figure 3B:
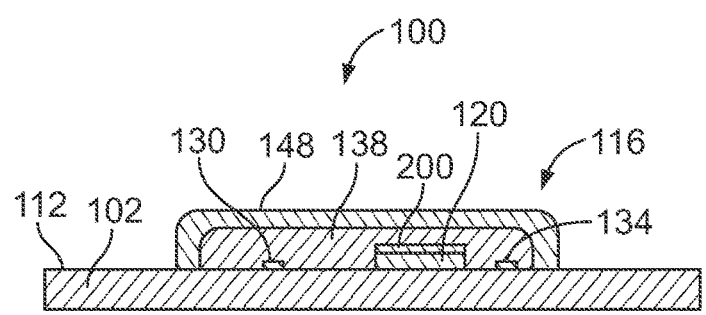
FIG. 3B is cross-sectional view taken along line C-C in FIG. 1 of the example substrate-based diagnostic device of FIG. 1.

FIG. 3B is a cross-sectional view of the example device 100 taken along line C-C of FIG. 1. In the illustrated example, the first electrode 120 is disposed on the top surface 112 of the paper substrate 102. In some examples, the reagent 200 is disposed on the top surface of the first electrode 120. The layer 138 of hydrophilic ink of the detection zone 116 covers the electrode 120 and the surrounding area so that a fluid sample can mix with the reagent and contact the first electrode 120. The capping layer 148 covers the top and sides of the layer 138 of hydrophilic ink and, thus, creates a leak-free area that defined by the capping layer 148 (e.g., the upper boundary) and the top surface 112 of the paper substrate 102 (e.g., the lower boundary). Also illustrated are the second and third traces 130, 134 that connect to the second and third contacts 132, 136, respectively (FIG. 1).

Figure 4:
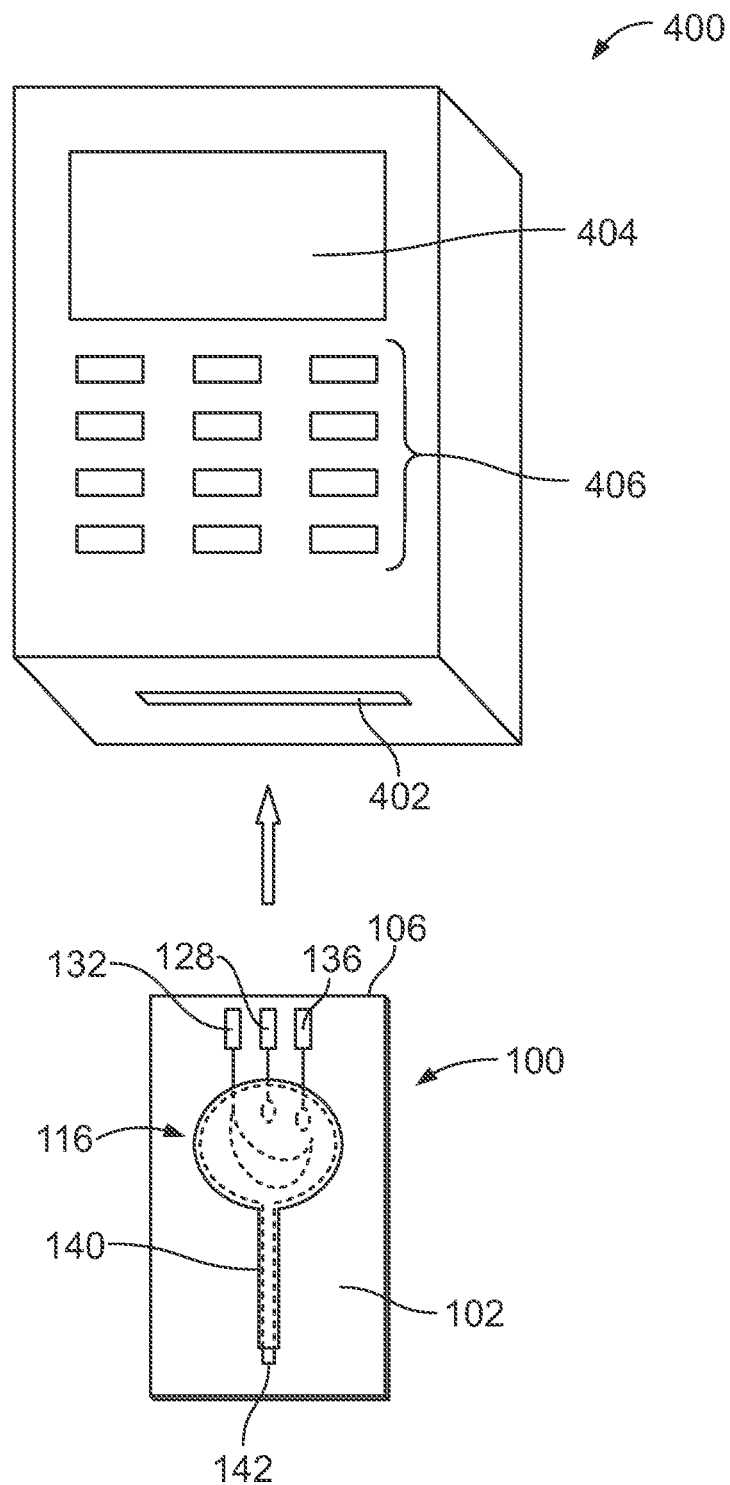
FIG. 4 is an example system including the example substrate-based diagnostic device of FIG. 1 and an example reader for use with the example substrate-based diagnostic device.

An example reader 400 for use with the example substrate-based diagnostic device 100 is illustrated in FIG. 4. After a sample is deposited onto the first end 142 of the channel 140, wicked through the channel 140 and the layer 138 into the detection zone 116 and mixed with the reagent 200, the electrical signals produced by the reaction may be read. To read the signals, the second end 106 of the paper sheet 102 may be inserted into a slot 402 in the reader 400. The slot includes a plurality (e.g., three) of pins (or contact points) that engage the first, second, and third contacts 128, 132, 136. In the illustrated example, the reader 400 includes a screen 404 (e.g., a user interface, a display screen, etc.) and a plurality of buttons 406 for interacting with the screen 404. In the illustrated example, the reader 400 detects the analyte of interest using, for example, amperometric, voltammetric, and/or potentiometric techniques. For example, the reader 400 may measure (e.g., via a processor) the difference in voltage between the first electrode 120 and the second electrode 122 pair (e.g., the working/counter electrode pair) and the third electrode 124 and the second electrode 122 pair (e.g., the reference/counter electrode pair). The difference in voltage between the two pairs may be correlated with the presence, absence, and/or concentration of the target analyte. In some examples, the device 100 includes a plurality of electrodes that form various sensors to detect analytes in the sample. In such an example, the reader may include additional pins to engage the additional contacts and the reader 400 may perform various measurements in sequence and/or simultaneously.

Figure 5:
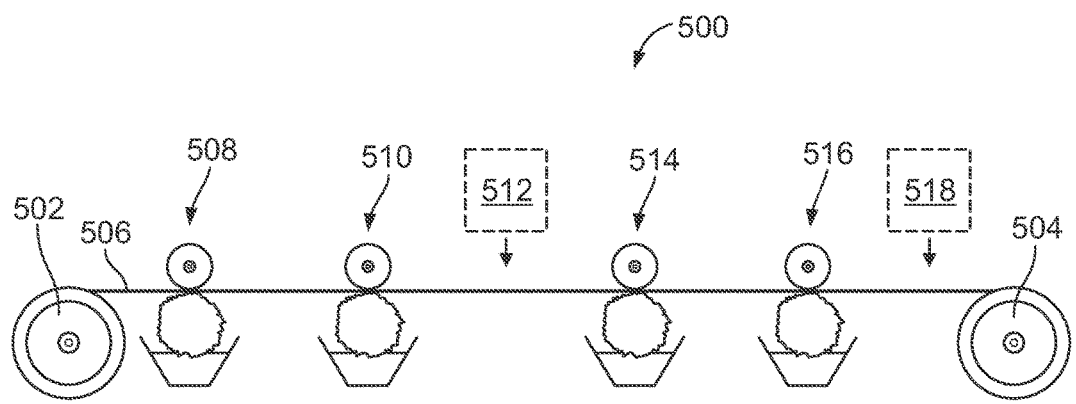
FIG. 5 is a diagram of an example assembly for constructing the example substrate-based diagnostic device of FIG. 1.

FIG. 5 is a diagram of an example system or assembly 500 for creating (e.g., manufacturing, fabricating, constructing)

a substrate-based diagnostic device such as, for example, the example device 100 of FIG. 1. The assembly 500 includes a series or a plurality of rollers, including a first roller 502 and a second roller 504, which operate in synchronized rotation to drive a substrate 506 through the assembly 500. In some examples, the assembly 500 includes additional rollers to move the base substrate 506 through the assembly using web-fed continuous processing or roll-to-roll techniques. Other examples may use conveyors, pulleys and/or any other suitable transport mechanism(s).

In the example assembly 500, the first roller 502 rotates to unwind the substrate 506, which, in some examples, is a single sheet in a rolled configuration. In the illustrated example, the substrate 506 is a hydrophobic (e.g., fluid impermeable) sheet of paper such as, for example, the paper substrate 102 (FIGS. 1 and 2A). In some examples, the substrate 506 is manufactured from materials (e.g., tree pulp) and/or chemicals that result in a hydrophobic paper substrate. In other examples, the substrate 506 begins as traditional paper and is then treated with wax or additional coatings/layers to create a hydrophobic surface. In some examples, the substrate 506 is a continuous roll of hydrophobic paper. However, in other examples, the substrate 506 may be die cut, perforated or serrated into defined or distinct sheets or strips (e.g., which then become individual diagnostic devices).

In the illustrated example of FIG. 5, the assembly 500 includes a first printing station 508 and a second printing station 510 for printing electrodes (e.g., the electrodes 120, 122, 124) onto the substrate 506 (e.g., onto the top surface of the substrate 506). In the illustrated example, the first printing station 508 prints a first type of electrode (e.g., having Ag/AgCl) onto the substrate 506 and the second printing station 510 prints a second type of electrode (e.g., having Au) onto the substrate 506. In some examples, two or three electrodes are printed onto the substrate 506. For example, a first electrode may be a working electrode made of Au and a second electrode may be a counter electrode made of Au. Additionally, a third electrode may be a reference electrode made of Ag/AgCl. In such an instance, the first printing station 508 may include Au ink to print the first and second electrodes and the second printing station 510 may include Ag/AgCl ink to print the third electrode. In other examples, the first and second printing stations 508, 510 are interchanged.

In the illustrated example, the first and second printing stations 508, 510 are rotary screen printers. In general, a rotary screen printer utilizes a screen having an image (e.g., a negative of the shape) curved around a cylinder. As the image of the screen is rotated into contact with a substrate, an ink passes through the holes of the screen and is imprinted onto the substrate. The screens of the rotary screen printers 508, 510 may include the shapes of the electrodes that are to be deposited onto the base substrate 506. As the cylinders rotate, ink fills into the negative image on the screen and the image (e.g., the electrode(s)) is printed onto the base substrate 506. For example, the device 100 of FIG. 1 includes the first, second and third electrodes 120, 122, 124, which are deposited onto the top surface 112 of the paper substrate 102. An example cross-sectional view of the paper substrate 102 having the electrodes is illustrated in FIG. 2B.

In some examples, the first and second printing stations 508, 510 also print traces (e.g., wires, leads) and contacts onto the substrate 506. The contacts may be used for communicatively coupling the electrodes to a reader, as disclosed above. For example, the device 100 of FIG. 1 includes the first, second and third contacts 128, 132, 136, and the first, second and third traces 126, 130, 134, and an example cross-sectional view of the device 100 at such a printing step is illustrated in FIG. 2C.

In some examples, only one electrode is printed onto the substrate 506. In other examples, more than one electrode is printed onto the substrate 506. In some examples, all of the electrodes are printed onto the substrate 506 at the same printing station. In other examples, multiple printing stations are utilized for printing multiple electrodes and/or producing electrodes with multiple layers.

In some examples, a reagent is deposited onto one or more of the electrodes via an optional third printing station 512 (shown in dashed lines). The third printing station 512 employs an inkjet printer to deposit one or more reagents. In other examples, the reagent(s) are printed directly onto the top surface of the substrate 506 (e.g., near the electrode(s)). For example, the device 100 includes the layer of reagent 200 (FIG. 2D) that is disposed on top of the first electrode 120 (e.g., the working/active electrode). The reagent 200 is illustrated in the cross-sectional views in FIGS. 2D-2F.

In the example assembly 500 of FIG. 5, a layer of suspension material or hydrophilic ink (e.g., the layer 138) and a channel of suspension material or hydrophilic ink (e.g., the channel 140) are deposited onto the substrate 506 at a fourth printing station 514. The ink used in the layer and the channel may include a suspension of hydrophilic particles (e.g., micro-beads or nano-beads) mixed with a binder. The layer is printed over the electrodes (and the reagent) and onto the surface of the substrate 506 between the electrodes. In the illustrated example, the fourth printing station 514 is rotary screen printer. The screen of the rotary screen printer may include a negative image of the channel and layer that is to be printed onto the substrate 506.

In some examples, the channel and the layer of the assembly 500 are printed onto the substrate 506 at the same time. In other examples, the assembly 500 includes multiple printing stations and the channel and the layer may be printed separately and/or by multiple printing steps.

In the illustrated example, a capping layer (e.g., the capping layer 148 of FIG. 1) is deposited over the layer and the channel at a fifth printing station 516. The capping layer is a hydrophobic ink, which creates a fluid-impermeable layer over the layer and the channel of the hydrophilic ink. In some examples, the capping layer is deposited over only the hydrophilic layer and the channel and is not deposited onto the rest of the substrate 506. As a result, less hydrophobic ink is used and, thus, reduces the cost of manufacturing.

In some examples, the base substrate 506 is diced or otherwise cut or separated into individual devices at an optional dicing station 518 (shown in dashed lines). In other examples, the dicing station 518 only creates a serration between two devices. In such an instance, the devices can be separated at a later time and/or in a different facility.

The example assembly 500 of the illustrated example utilizes a reel-to-reel (R2R) (e.g., web-fed continuous processing, roll-to-roll) process where the substrate 506 is unrolled from the first roller 502 and is rerolled onto the second roller 504 at the opposite end of the process. However, in other examples, other types of printing processes may be utilized.

Figure 6:
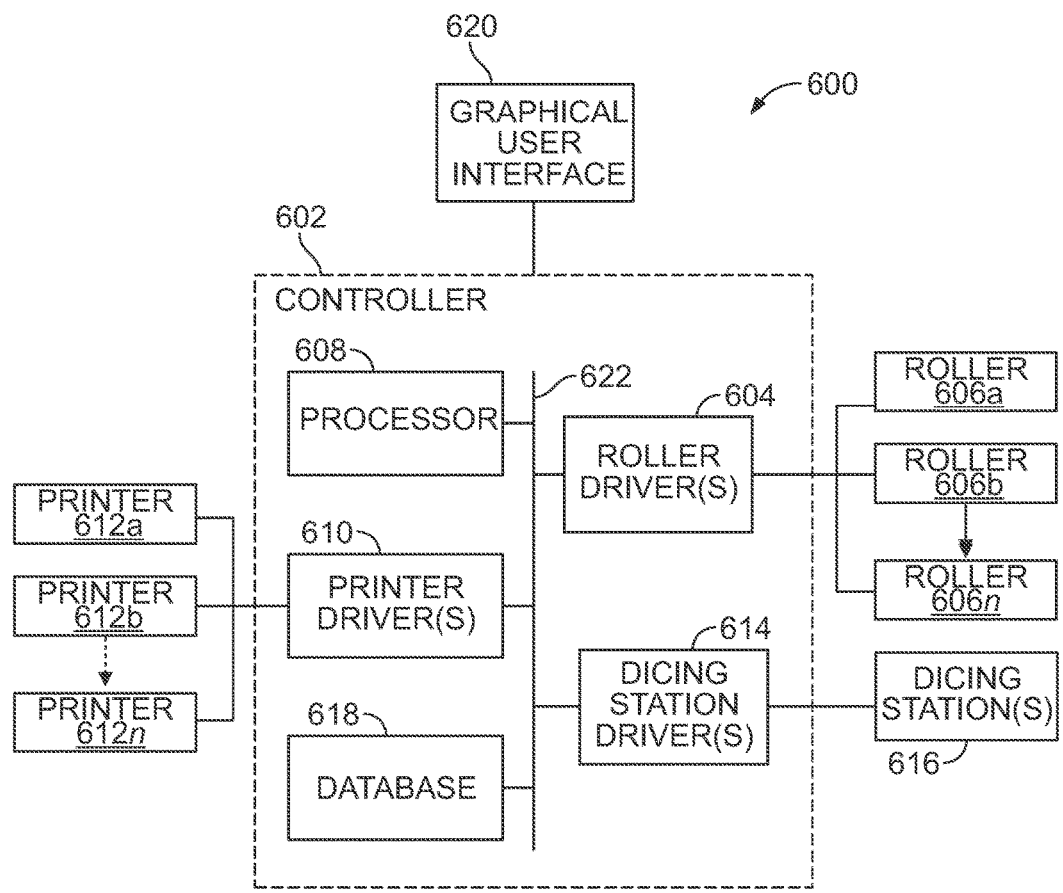
FIG. 6 is a block diagram of an example processing system for the example assembly of FIG. 5.

FIG. 6 is a block diagram of an example processing system 600 for use with a substrate-based diagnostic device fabrication assembly such as, for example, the assembly 500 of FIG. 5 to create, for example, the paper device 100 of FIG. 1. The example processing system 600 includes a controller 602, which controls operation of the assembly 500 via selected driver components.

For example, the processing system 600 includes a roller driver 604, which controls one or more rollers (e.g., the first and second rollers 502, 504) of the assembly 500. In some examples, the processing system 600 includes one or more roller drivers 604. In the example shown, the roller driver(s) 604 are communicatively coupled to one or more rollers 606a-n. The rollers 606a-n may correspond to, for example, the first and second rollers 502, 504 of the example assembly 500. In some examples, additional rollers (e.g., the rollers of the individual printing stations) are utilized in the assembly and the roller driver(s) 604 control the respective rollers 606a-n. The roller driver(s) 604 control rotation of the rollers 606a-n using, for example, a motor, to regulate one or more operational characteristics of the rollers. Such operational characteristics may include speed of rotation, duration of rotation, direction of rotation, acceleration, etc. of the rollers 606a-n. For example, speed of rotation can be used to determine a duration for which a portion of the substrate is exposed to one or more printing stations (e.g., one or more of the printing stations 508-514). Thus, the roller driver(s) 604 control the rate at which the one or more substrates are processed. In the illustrated example, a processor 608 operates the roller driver(s) 604 and, thus, the rollers 606a-n in accordance with a roller protocol.

In the illustrated example of FIG. 6, the processing system 600 includes a printer driver 610 which controls one or more of the printers of the assembly 500. In some examples, the example processing system 600 includes one or more printer drivers 610. In the example shown, the printer driver(s) 610 are communicatively coupled to one or more printers 612a-n. The printers 612a-n may correspond, for example, to the printers 508-514 of the example assembly 500. The printer driver(s) 612a-n control, for example, the thickness, the width, and/or the pattern of the electrode(s), the contact(s), the trace(s), the hydrophilic channel, the hydrophilic layer, and/or the capping layer material applied to the substrate 506 by the respective printing stations 508-514. In examples where ink (e.g., the conductive ink of the electrode(s), the hydrophilic ink of the layer and channel, the hydrophobic ink of the capping layer) is applied via rotary screen printing, the printer driver(s) 610 can control a pressure of the rollers associated with the respective printers 508, 510, 514, 516 and, thus, affect the quality of the ink applied to the substrate. In some examples, the printers 612a-n operate in connection with the rollers 606a-n. In such examples, the printer driver(s) 610 work in association with the roller driver(s) 604 to define, for example, a rate at which the electrode(s), the channel, the layer, and the capping layer are deposited onto the substrate. The illustrated example, the processor 608 operates the printer driver(s) 610 and, thus, the printers 612a-n in accordance with a conductive ink, hydrophilic ink, and/or hydrophobic ink application protocol.

The example processing system 600 also includes a dicing station driver 614 that controls a dicing station 616. In some examples, the example processing system 600 includes one or more dicing station drivers 614. In the example shown, the dicing station driver(s) 614 are communicatively coupled to one or more dicing station(s) 616. The dicing station(s) 616 may correspond to, for example, the dicing station 518 of the example assembly 500. The dicing station driver(s) 614 control, for example, the cutting or splitting of the substrates (e.g., into the individual paper substrate diagnostic devices), a size of the discrete units into which the substrates are cut, a spacing between discrete units formed from the continuous substrates, an operational speed of a cutting instrument, retraction of the cutting instrument, etc. In the illustrated example, the processor 608 operates the dicing station driver(s) 614 and, thus, the dicing station(s) 616 in accordance with a substrate dicing protocol.

In the illustrated example of FIG. 6, the processing system 600 includes a database 618 that may store information related to, for example, the operation of the example system 500. The information may include, for example, information about the length and dimensions of the substrates to be fed through the assembly 500; the materials and patterns of the electrodes, the contacts, the traces, the hydrophilic layers, the hydrophilic channels, the capping layers, and/or the reagents; rotational characteristics of the rollers, such as a speed and/or diameter; properties of the conductive, hydrophobic, hydrophilic, adhesive, and/or other material(s) to be applied to the substrates, etc.

The example processing system 600 of FIG. 6 includes a user interface such as, for example, a graphical user interface (GUI) 620. An operator or technician interacts with the processing system 600 and, thus, the example assembly 500 via the interface 620 to provide, for example, commands related to operation of the rollers 606a-n such as speed, duration of rotation, etc. of the rollers; the pattern(s) to be deposited via the printers 612a-n; materials and patterns of the electrodes, the contacts, the traces, the hydrophilic layers, the hydrophilic channels, the capping layers, and/or the reagents; the size of the discrete units into which the substrates are cut via the dicing station 616; etc. The interface 620 may also be used by the operator to obtain information related to the status of any substrate processing completed and/or in progress, check parameters such as speed and alignment, and/or to perform calibrations.

In the illustrated example, the processing system components 604, 608, 610, 614, 618 are communicatively coupled to other components of the example processing system 600 via communication links 622. The communication links 622 may be any type of wired connection (e.g., a databus, a USB connection, etc.) and/or any type of wireless communication (e.g., radio frequency, infrared, etc.) using any past, present or future communication protocol (e.g., Bluetooth, USB 2.0, USB 3.0, etc.). Also, the components of the example system 600 may be integrated in one device or distributed over two or more devices.

Figure 7:
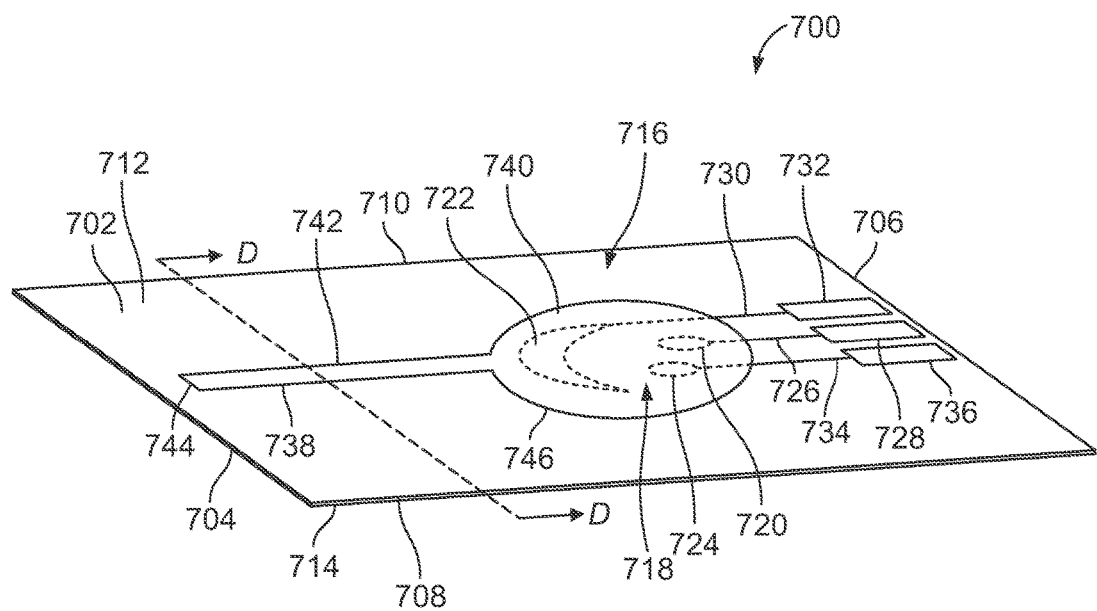
FIG. 7 is a perspective view of an alternative example substrate-based diagnostic device constructed in accordance with the teachings of this disclosure.

FIG. 7 illustrates another example substrate-based diagnostic device 700 (e.g., a paper-based detection device) that may be used for IA or CC testing. Similar to the device 100 disclosed above, the device 700 includes a detection zone, a channel and a capping layer. However, in the device 700, the detection zone and the channel are defined within the material of the substrate, which is hydrophilic, by barriers of hydrophobic ink printed into the substrate.

For example, in the illustrated example of FIG. 7, the device 700 includes a substrate 702, which is implemented as a hydrophilic piece of paper. In other words, the substrate 702 is porous and is capable of absorbing and/or retaining liquids. In the illustrated example, the paper substrate 702 has a first end 704, a second end 706 opposite the first end 704, a first side 708, a second side 710 opposite the first side 708, a top surface 712 and a bottom surface 714 opposite the top surface 712. In the illustrated example, the paper substrate 702 is substantially rectangular. However, in other examples, the paper substrate 702 may be in another shape such as, for example, a square, a triangle, a circle, an ellipse, an irregular shape, etc.

In the illustrated example, the device 700 includes a detection zone 716 (e.g., a test area, a reaction zone, etc.)

that defines a location where the test is to occur. The detection zone 716 has a sensor 718 for detecting a reaction between the sample and a reagent, which is then used to measure the presence, absence and/or concentration of the target analyte in the sample. In the illustrated example, the sensor 718 includes a first electrode 720 (e.g., a working electrode), a second electrode 722 (e.g., a counter-electrode, a ground electrode) and a third electrode 724 (e.g., a reference electrode). The first, second and third electrodes 720, 722, 724 may operate similar to the first, second and third electrodes 120, 122, 124 of the example device 100. In the illustrated example, however, the first, second, and third electrodes 720, 722, 724 are printed into the material of the substrate 702. Because the substrate 702 is hydrophilic, the conductive ink of the first, second, and third electrodes 720, 722, 724 is absorbed into the material of the substrate 702. In some examples, the one or more of the electrodes 720, 722, 724 are made of gold (Au), gold on silver chloride (AgCl), carbon (C), and/or silver/silver chloride (Ag/AgCl). The one or more of the electrodes 720, 722, 724 may be printed onto the substrate 702 using, for example, gravure printing, flexographic printing, screen printing, rotary screen printing, and/or inkjet printing. In other examples, other suitable types of printing processes may be employed to print the conductive ink onto the paper substrate 702.

In the illustrated example of FIG. 7, the device 700 includes a first trace 726 that electrically couples the first electrode 720 to a first contact 728, a second trace 730 that electrically couples the second electrode 722 to a second contact 732, and a third trace 734 that electrically couples the third electrode 724 to a third contact 736. The device 700 may be used by an electric reader (e.g., the reader 400) and the contacts 728, 732, 736 enable the reader to electrically communicate with the electrodes 720, 722, 724 and sense electrical signals including, for example, changes in, for example, amps, volts and/or resistance.

To create a boundary for the detection zone 716 and/or a channel to wick sample the detection zone 716, the device 700 includes a hydrophobic barrier 738. The hydrophobic barrier 738 is a line of hydrophobic ink that is printed into the substrate 702 and forms or defines a pathway therebetween. To enable the sample to come into contact with the electrodes 720, 722, 724 in the substrate 702, a layer 740 of hydrophilic mesh (e.g., hydrophilic ink of material suspension) is deposited onto the substrate 702 at the detection zone 716. The hydrophilic mesh absorbs into the material of the paper substrate 702. The hydrophilic mesh may include hydrophilic ink similar to that of the layer 138 disclosed above. The hydrophilic mesh has increased wicking capabilities to wick a sample through the detection zone 716. Additionally, in the illustrated example a channel 742 of the hydrophilic mesh is deposited into the material of the paper substrate 702 to form a channel from the first end 704 of the paper substrate 702 to the layer 740. The hydrophilic mesh absorbs into the material of the paper substrate but is bounded by the hydrophobic barrier 738. In other words, the hydrophilic mesh may be printed onto the paper substrate 702, and the hydrophobic barrier 738 prevents the hydrophilic ink from spreading out beyond the hydrophobic barrier 738. The hydrophilic mesh of the layer 740 and the channel 742 may include hydrophilic ink similar to that of the layer 138 and channel 140 disclosed above in connection with the device 100. The hydrophobic mesh or the layer 740 and/or the channel 742 may be printed onto the substrate 702 using a printing process such as, for example, gravure printing, flexographic printing, screen printing, rotary screen printing, and/or inkjet printing.

Figure 8:
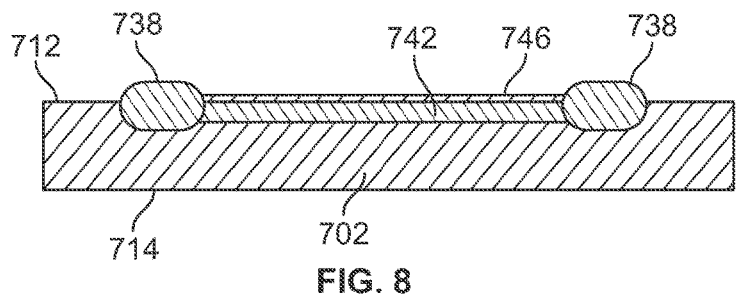
FIG. 8 is a cross-sectional view taken along line D-D in FIG. 7 of the example substrate-based diagnostic device of FIG. 7.

FIG. 8 is a cross-sectional view of the example device 700 taken at line D-D of FIG. 7. In the illustrated example, the hydrophobic barrier 738 is printed onto the paper substrate 702 and is absorbed into the material of the paper substrate 702. The hydrophobic barrier 738 repels or resists liquid and, thus, creates a pathway between the lines of the hydrophobic barrier 738. Particularly, when the hydrophilic mesh is printed onto the paper substrate, the hydrophilic ink absorbs into the material of the paper substrate but is bounded between the hydrophobic barrier 738. When a fluid sample is deposited (e.g., pipetted) at an inlet 744 (FIG. 7) of the channel 742, the sample wicks (e.g., via capillary action) through the hydrophilic mesh (e.g., the porous cellulose matrix) of the channel 142, between the lines of the hydrophobic barrier 738, and into the hydrophilic mesh of the layer 740. In this manner, the sample is transferred through the channel 742 and into the detection zone 716 where the sample contacts or wets the electrodes 720, 722, 724.

In some examples, the hydrophobic ink of the hydrophobic barrier 738 is printed using a printing process such as, for example, gravure printing, flexographic printing, screen printing, rotary screen printing, and/or inkjet printing. In other examples, other suitable types of printing processes may be employed to print the hydrophobic ink onto the substrate 702. In some examples, the hydrophobic ink may be printed onto the substrate prior to printing the conductive inks of the sensor. For example, hydrophobic ink or barrier may be used to create a pattern for printing the electrodes 720, 722, 724, the traces 726, 730, 734 and/or the contacts 728, 732, 736. In some such examples, this results in increased adhesion of the conductive ink to the substrate 702.

In the illustrated example of FIG. 8, the hydrophobic barrier 738 is only disposed partially into the thickness of the substrate 702. However, in other examples, the hydrophobic barrier 738 is absorbed fully into the substrate 702. In both examples, the hydrophobic barrier 738 creates a barrier between two sections of the substrate 702.

In some examples, one or more reagents are printed into the paper substrate 702. For example, a reagent may be printed into the substrate 702 in the detection zone 716. As the sample wicks into the detection zone 716, the sample interacts with the reagent and the biomolecular interaction can be detected by the sensor 718. Additionally or alternatively, one or more reagents may be printed onto the first electrode 720. The reagent(s) may be printed using, for example, in-line inkjet printing or high-throughput (e.g., up to 120 meters/minute) printing such as, for example, flexographic printing, screen printing, or slot die deposition. In some examples, the reagent(s) may be embedded in a hydrogel or other polymer(s) and printed as a suspension that is later cured (e.g., via ultra-violet light or electropolymerization). In some examples, a plurality of electrodes are employed to perform different types of assays and the electrodes may be functionalized with different binding reagents to detect a plurality of analytes.

In some examples, a capping layer 746 is applied to the top surface 712 of the paper substrate 702 to prevent the evaporation of sample and/or reduce the risk of contamination. The capping layer 746 creates a fluid-impermeable (or hydrophobic) surface over the top of the hydrophilic mesh of the channel 742 and the layer 740 of the detection zone 716. In some examples, the capping layer 746 is a hydrophobic substrate (e.g., a sheet of hydrophobic paper) that is coupled (e.g., laminated, bonded) to the top surface 712 of the paper substrate 702. In some examples, the capping layer 746 is not disposed on top of the inlet 744 of the channel 742, so that the fluid sample may be deposited at the inlet 744 of the channel 742. In other examples, the entire channel 742 is covered with the capping layer and an opening or hole may be defined in the capping layer to allow the fluid sample to come into contact with the substrate 702 at the inlet 744 of the channel 742.

In the illustrated example, the hydrophilic mesh or ink is printed into the substrate 702 to form the channel 142 and layer 740. However, in other examples, a hydrophilic mesh is not used. Instead, the porous structure of the substrate 702 itself forms the channel 742 and layer 740. For example, a fluid may be wicked through the porous/hydrophilic structure of the substrate 702 between the barrier 738.

In some examples, the composition of the conductive ink(s), hydrophobic ink(s), the hydrophilic ink(s), and/or dielectric ink(s) may depend on the properties of the substrate 702 and/or the printing processes used. For example, the conductive ink may need to be cured or dried after deposition (e.g., via ultra-violet light, heat, infrared (IR), or air-drying) depending on the ink composition and/or the tolerances of the substrate.

Figure 9:
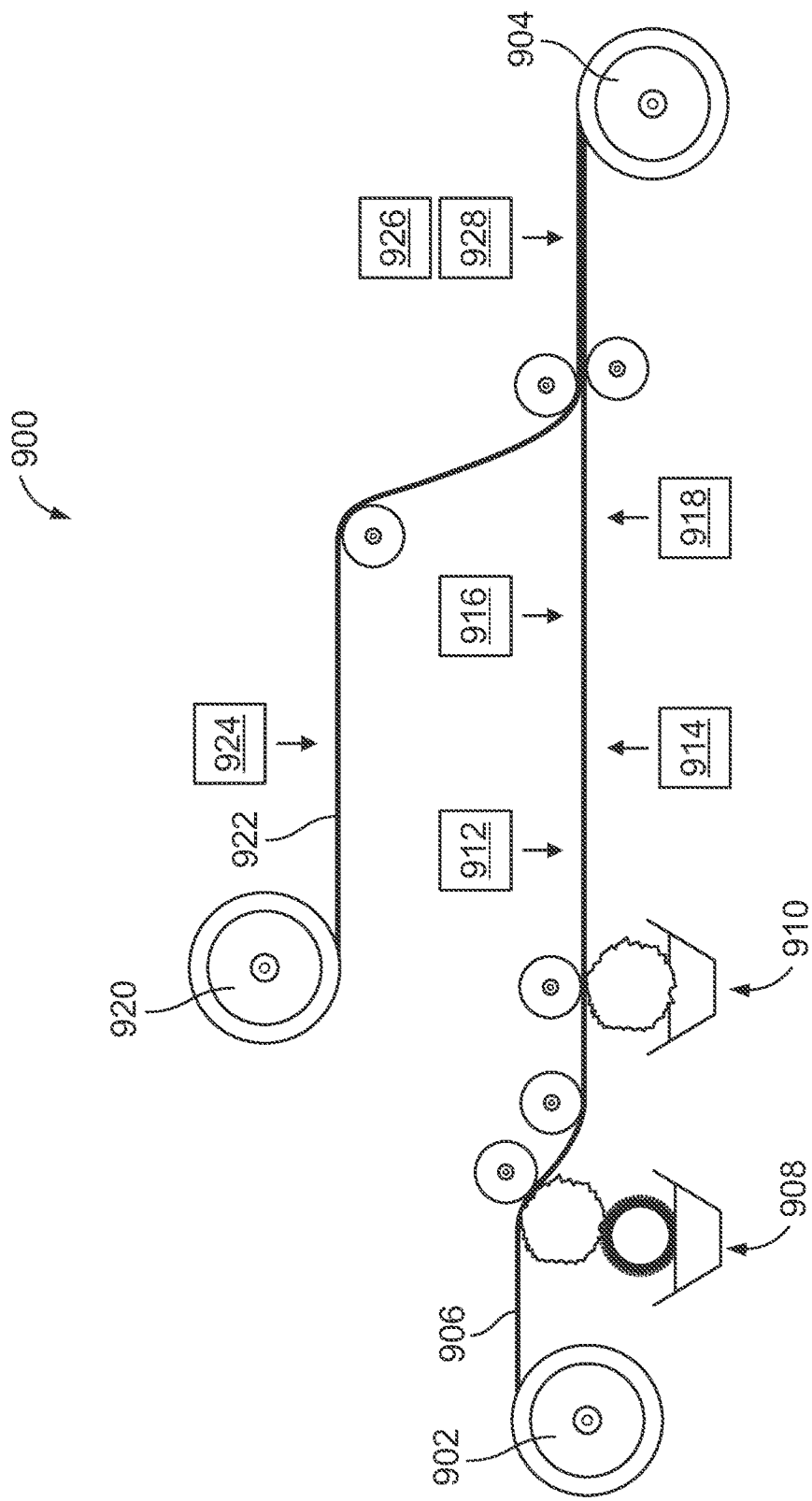
FIG. 9 is a diagram of an example assembly for creating the example substrate-based diagnostic device of FIG. 7.

FIG. 9 is a diagram of an example system or assembly 900 for creating (e.g., manufacturing, producing, making, constructing, fabricating) a paper substrate diagnostic device such as, for example, the device 700 of FIG. 7. The assembly 900 includes a series or a plurality of rollers, including a first roller 902 and a second roller 904, which operate in synchronized rotation to drive a substrate 906 through the assembly 900. In some examples, the assembly 900 includes additional rollers to move the substrate 906 through the assembly using web-fed continuous processing or roll-to-roll techniques. Other examples may use conveyors, pulleys and/or any other suitable transport mechanism(s). In the illustrated example, a plurality of printing processes is provided to create one or more devices on the substrate 906, such that the devices can be mass-produced.

In the example assembly 900, the first roller 902 rotates to unwind the substrate 906, which, in some examples, is a single sheet in a rolled configuration. In the illustrated example, the substrate 906 is paper and is hydrophilic (e.g., having a strong affinity for liquid). In some examples, the substrate 906 is a continuous roll of hydrophilic paper. However, in other examples, the substrate 906 may be cut, serrated or otherwise separated into defined or distinct sheets or strips (e.g., which then become individual diagnostic devices). The substrate 906 may correspond, for example, to the paper substrate 702 of the device 700. An example cross-sectional view of the paper substrate 702 is illustrated in FIG. 8.

In the illustrated example, the assembly 900 includes a first printing station 908 for printing a barrier of hydrophobic ink onto the substrate 906. The hydrophobic ink is printed onto the substrate 906 to define a pathway and detection zone for testing. Once dried, the hydrophobic ink creates a barrier (e.g., the barrier 738) that prevents a sample from wicking or absorbing into the substrate in areas outside of the defined pathway and detection area. In the illustrated example, the printing station 908 is a flexographic printer. In general, flexographic printing involves the use of a relief plate. In the illustrated example, the plate is wrapped around a roller, so that as the roller rotates it deposits an image (e.g., the lines defining the channel and the detection zone) on the substrate 906. Additionally or alternatively, other types of printing processes may be implemented to print the hydrophobic ink such as, for example, gravure printing, screen printing, rotary screen printing, or inkjet printing.

In the illustrate example, the assembly 900 includes a second printing station 910 and a third printing station 912 for printing electrodes onto the substrate 906. In the illustrated example, the second printing station 910 prints a first type of electrode (e.g., having Ag/AgCl) onto the substrate 906 and the third printing station 912 prints a second type of electrode (e.g., having AuNP) onto the base substrate 906. In some examples, two or three electrodes are printed onto the substrate 906. For example, a first electrode may be a working electrode made of AuNP and a second electrode may be a counter electrode made of AuNP. In addition, a third electrode may be a reference electrode made of Ag/AgCl. In such an instance, the third printing station 912 may include AuNP ink to print the first and second electrodes and the second printing station 910 may include Ag/AgCl ink to print the third electrode. In other examples, the second and third second printing stations 910, 912 are interchanged. In the illustrated example, the second printing station 910 is rotary screen printer and the third printing station 912 is an inkjet printing. However, in other examples, other types of printing processes may be implemented to print the electrodes onto the substrate 906. The electrodes may correspond, for example, to the first, second, and third electrodes 720, 722, 724 of the device 700.

The conductive ink for the electrodes is deposited onto the substrate 906 and is absorbed into the material of the substrate 906. Thus, in the illustrated example, the electrodes are at least partially disposed within the material of the substrate 906. In some examples, the second and third printing stations 910, 912 also print traces (e.g., wires, leads) and contacts onto the substrate 906. The contacts may be used for connecting the diagnostic device with a reader, such that the reader includes pins or contacts that mate with the contacts on the device. For example, the device 700 of FIG. 7 includes the first, second and third contacts 728, 732, 736, and the first, second and third traces 726, 730, 734.

In some examples, only one electrode is printed onto the substrate 906. In other examples, more than one electrode is printed onto the base substrate 906. In some examples, all of the electrodes are printed onto the substrate 906 at the same printing station. In other examples, multiple printing stations are utilized for printing multiple electrodes and/or producing electrodes with multiple layers.

In the illustrated example, the assembly 900 includes a sintering station 914 for sintering one or more of the electrodes. In general, sintering is a process for forming a solid mass of material by heat and/or pressure. The sintering process causes the atoms of the material to diffuse across the boundaries of the particles, fusing the particles together and creating one solid piece. The sintering station 914 may include a heat and/or pressure source to sinter (e.g., fuse together) the material of each one of the electrodes. The sintering station 914 may operate by applying alternating current or direct current to the electrode(s) to induce coalescence of the conductive material.

In the illustrated example, the assembly includes a fourth printing station 916 for depositing one or more reagents onto the electrodes or around the electrodes on the substrate 906. In the illustrate example, the fourth printing station 916 is inkjet printer. Additionally or alternatively, other types of printing processes may be implemented to deposit one or more reagents onto the substrate 906 such as, for example, flexographic printing, screen printing, or slot die deposition.

In some examples, a hydrophilic mesh layer is deposited (e.g., printed) onto the substrate 906 at the channel (e.g., the channel 742) and detection zone (e.g., the detection zone 740) areas to increase the ability of the sample to wick through the substrate 906. In the illustrated example, the assembly 900 includes a fifth printing station or mesh lamination station 918 that deposits (e.g., prints and fixes) a hydrophilic ink onto the substrate 906. The hydrophilic ink permeates or absorbs into the material of the substrate 906 between the hydrophobic barrier to create the channel and the detection zone. In some examples, the mesh lamination station 918 includes a printer such as, for example, a gravure printer, a flexographic printer, a screen printer, a rotary screen printer, and/or an inkjet printer.

In the illustrated example, a capping layer (e.g., the capping layer 746 of FIG. 7) is disposed over the substrate 906 to seal the channel and the detection zone to reduce the likelihood of evaporation of the sample and/or contamination. In the illustrated example, the assembly 900 includes a third roller 920 that unwinds a hydrophobic (e.g., fluid impermeable) substrate 922. The hydrophobic substrate 922 may be, for example, a hydrophobic sheet or piece of paper. The hydrophobic substrate 922 is laminated onto the top of the substrate 906 to seal the channel and the detection zone of the device. As a result, a substantially fluid sealed pathway is created in the substrate 906 between the hydrophobic barrier and the capping layer.

In the illustrated example, the assembly 900 includes a laser 924 (e.g., a $CO_2$ laser, an excimer laser) for cutting the hydrophobic substrate 922 into a specific pattern and/or creating sample and/or reagent inlet ports in the hydrophobic substrate 922. For example, the laser 924 may change the hydrophobicity of the hydrophobic substrate 924 in certain areas to create sample and/or reagent inlet ports. The laser modifies the hydrophobicity of the hydrophobic substrate 922 and increases the ability of the hydrophobic substrate 922 to absorb and/or wick fluids (e.g., samples and/or reagents). When the hydrophobic substrate 922 is coupled to the top of the substrate 906, the hydrophobic substrate 922 forms a fluid impermeable cap over the device, and the sample and/or reagent inlet ports enable samples and/or reagents to be deposited into the device (e.g., through the hydrophobic substrate 922). In some examples, the extent of the hydrophilicity can be modified by changing the extent of laser processing of the hydrophobic substrate. In this manner, valve structures can be created to control the flow of samples and/or reagent into and/or through the device. In some examples, the hydrophobic substrate 906 is cut or formed into a shape matching that of the channel and the detection zone, such that only the channel and the detection zone are capped. As a result, less material may be used when forming the capping layer.

In some examples, instead of using the hydrophobic substrate 922, a layer of hydrophobic ink is printed over onto the substrate 906 to form the capping layer. In some examples, the hydrophobic ink is printed only on top of the channel and the detection zone.

In the illustrated example, the assembly 900 includes a lamination unit 926 for coupling the hydrophobic substrate 922 to the top of the substrate 906. The lamination unit 926 may include a heat and/or pressure source for adhering the two substrates 906, 922 together. In some examples, and adhesive (e.g., a glue) may be utilized. In some examples, multiple additional sheets of impermeable paper may be used to create a multilayered laminated device.

In some examples, the substrate 906 is diced or otherwise separated into individual devices. The example assembly 900 includes a dicing station 928 that cuts the substrate 906 into the individual devices. In other examples, the dicing station 926 creates a serration between two devices. In such an instance, the devices can be separated at a later time and/or in a different facility.

The assembly 900 of the illustrated example utilizes a reel-to-reel (R2R) (e.g., web-fed continuous processing, roll-to-roll) process where the substrate 906 is unrolled from the first roller 902 and is rerolled onto the second roller 904 at the opposite end of the process. The substrate 906 at the second roller 904 has a plurality of microfluidic diagnostic devices printed onto the substrate 906. The device may correspond, for example, the device 700 of FIG. 7.

Figure 10:
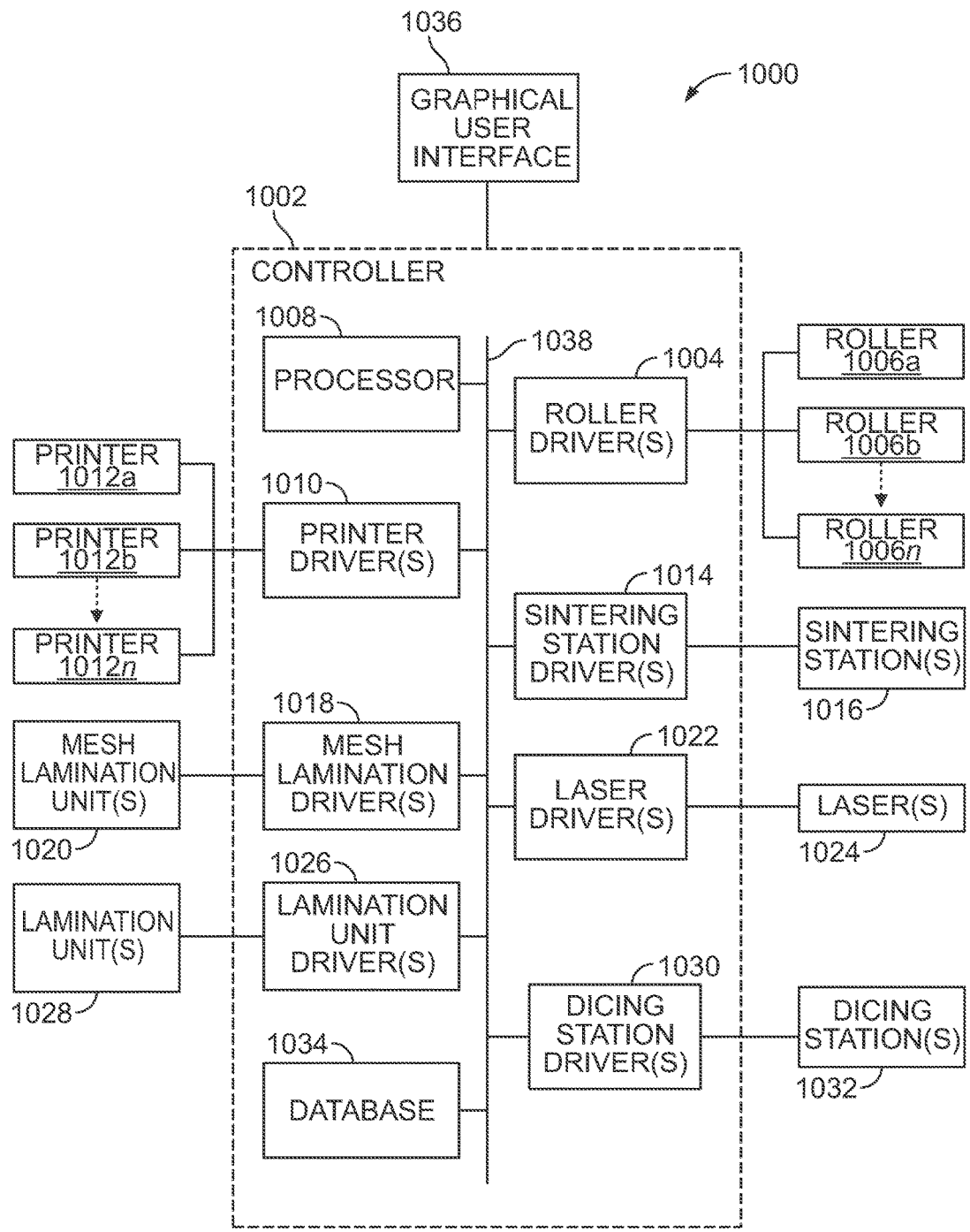
FIG. 10 is a block diagram of an example processing system for the example assembly of FIG. 9.

FIG. 10 is a block diagram of an example processing system 1000 for use with a substrate-based diagnostic device fabrication assembly such as, for example, the assembly 900 of FIG. 9. The example processing system 1000 includes a controller 1002, which controls operation of the assembly 900 via selected driver components.

For example, the example processing system 1000 includes a roller driver 1004, which controls one or more of the rollers (e.g., the first, second and/or third rollers 902, 904, 920) of the assembly 900. In some examples, the processing system 1000 includes one or more roller drivers 1004. In the example shown, the roller driver(s) 1004 are communicatively coupled to rollers 1006a-n. The rollers 1006a-n may correspond, for example, to the first, second, and third rollers 902, 904, 920 of the example assembly 900. In some examples, additional rollers (e.g., the rollers of the individual printing stations) are utilized in the assembly and the roller driver(s) 1004 control the respective rollers 1006a-n. The roller driver(s) 1004 control rotation of the rollers 1006a-n using, for example, a motor, to regulate one or more operational characteristics of the rollers. Such operational characteristics may include speed of rotation, duration of rotation, direction of rotation, acceleration, etc. of the rollers 1006a-n. For example, speed of rotation can be used to determine a duration for which a portion of the substrate is exposed to one or more printing stations (e.g., one or more of the printing stations 908, 910, 912, 916). Thus, the roller driver(s) 1004 control the rate at which the one or more substrates are processed. Also, an example processor 1008 operates the roller driver(s) 1004.

The example processing system 1000 includes a printer driver 1010 which controls one or more of the printers of the assembly 900. In some examples, the example processing system 1000 includes one or more printer drivers 1010. In the example shown, the printer driver(s) 1010 are communicatively coupled to printers 1012a-n. The printers 1012a-n may correspond, for example, to the printers 908, 910, 912, 916 of the example assembly 900. The printer driver(s) 1012a-n control, for example, the thickness, width, and/or pattern of the electrode(s), contact(s), trace(s), hydrophilic barrier, and/or reagent(s) applied to the substrate 906 by the printing stations 908, 910, 912, 916. In examples where ink (e.g., the conductive ink of the electrode(s), the hydrophobic ink of the hydrophobic barrier) is applied via rotary screen printing or flexographic printer, the printer driver(s) 1010 can control a pressure of the rollers associated with the respective printers 908, 910 and, thus, affect the quality of the ink applied to the substrate. In some examples, the printers 908, 910, 912, 916 operate in connection with the rollers 902, 904, 920. In such examples, the printer driver(s) 1010 work in association with the roller driver(s) 1004 to define, for example, a rate at which the electrode(s), the reagent(s), the hydrophobic barrier, etc. are deposited onto the substrate. In the illustrated example, the processor 1008 operates the printer driver(s) 1010 and, thus, the printers 1012*a-n* in accordance with a conductive ink, hydrophobic ink, and/or reagent ink application protocol.

The example processing system 1000 includes a sintering station driver 1014 that controls the sintering station of the example assembly 900. In some examples, the processing system 1000 includes one or more sintering station drivers 1014. In the illustrated example, the one or more sintering station driver(s) 1014 are communicatively coupled to one or more sintering station(s) 1016. The sintering station(s) 1016 may correspond, for example, to the sintering station 914 of the example assembly 900. The sintering station driver(s) 1014 may control, for example, the intensity of pressure and/or heat applied to the substrate, the size of an area of the substrate exposed to the pressure and/or heat, a duration of exposure of the pressure and/or heat, etc. In the illustrated example, the processor 1008 operates the sintering station driver(s) 1014 and, thus, the sintering station(s) 1016 in accordance conductive ink and/or dielectric ink application protocol.

The example processing system 1000 includes a mesh lamination driver 1018 that controls the mesh lamination unit of the example assembly 900. In some examples, the processing system 1000 includes one or more mesh lamination drivers 1018. In the illustrated example, the one or more mesh lamination driver(s) 1018 are communicatively coupled to one or more mesh lamination unit(s) 1020. The mesh lamination unit(s) 1020 may correspond, for example, to the mesh lamination unit 918 of the example assembly 900. The mesh lamination driver(s) 1018 may control, for example, the thickness, width, and/or pattern of the hydrophilic ink or mesh layer applied to the substrate 906 by the mesh lamination unit 918. In some examples, the mesh lamination unit 1020 is implemented as a printer and may be controlled, for example, by the printer driver(s) 1010. In the illustrated example, the processor 1008 operates the mesh lamination driver(s) 1018 and, thus, the mesh lamination unit(s) 1020 in accordance with a mesh layer and/or hydrophilic ink application protocol.

The example processing system 1000 includes a laser driver 1022. In some examples, the example processing system 1000 includes one or more laser drivers 1022. In the example shown, the one or more laser driver(s) 1022 are communicatively coupled to one or more lasers 1024 to control the laser(s) 1024. The laser(s) 1024 may correspond to, for example, the laser 924 of the example assembly 900. The laser driver(s) 1022 control, for example, the intensity of the laser(s) 1024, a size of surface area of irradiation with respect to the substrate(s), the depth to which the laser(s) 1024 penetrate a substrate, a duration for which the laser(s) 1024 do or do not penetrate the substrate, and/or the extent to which the laser(s) 1024 affect or change the hydrophobicity of the substrate (e.g., the hydrophobic substrate 922). In the illustrated example, the processor 1008 operates the laser driver(s) 1022 and, thus, the laser(s) 1024 in accordance with a laser protocol.

The example processing system 1000 includes a lamination unit driver 1026. In some examples, the example processing system 1000 includes one or more lamination unit drivers 1026. In the illustrated example, the one or more lamination unit driver(s) 1026 are communicatively coupled to one or more lamination unit(s) 1028 to control the lamination unit(s) 1028. The lamination unit(s) 1028 may correspond to, for example, the lamination unit 926 of the example assembly 900. The lamination unit driver(s) 1026 control, for example, the intensity of pressure and/or heat applied to the substrate(s) (e.g., the hydrophobic substrate 922 and the substrate 906), the size of an area of the substrate(s) exposed to the pressure and/or heat, a duration of exposure of the pressure and/or heat, an amount of adhesive applied between the substrate(s), etc. In the illustrated example, the processor 1008 operates the lamination driver(s) 1026 and, thus, the lamination unit(s) 1028 in accordance with a lamination protocol.

The example processing system 1000 includes a dicing station driver 1030 that controls a dicing station 1032. In some examples, the example processing system 1000 includes one or more dicing station drivers 1030. In the example shown, the one or more dicing station driver(s) 1030 are communicatively coupled to one or more dicing station(s) 1032. The dicing station(s) 1032 may correspond to, for example, the dicing station 928 of the example assembly 900. The dicing station driver(s) 1030 control, for example, the cutting or splitting of the substrate(s) (e.g., into the individual paper substrate diagnostic devices), a size of the discrete units into which the substrates are cut, a spacing between discrete units formed from the continuous substrates, an operational speed of a cutting instrument, retraction of the cutting instrument, etc. In the illustrated example, the processor 1008 operates the dicing station driver(s) 1030 and, thus, the dicing station(s) 1032 in accordance with a substrate dicing protocol.

The example processing system 1000 includes a database 1034 that may store information related to, for example, the operation of the example system 1000. The information may include, for example, information about the length and dimensions of the substrate(s) (e.g., the substrate 906 and/or the hydrophobic substrate 922) to be fed through the assembly 900; the materials and patterns of the electrodes, the contacts, the traces, the hydrophobic barriers, the mesh layers or hydrophilic inks, the capping layers, and/or the reagents; rotational characteristics of the rollers, such as a speed and/or diameter; properties of the conductive, hydrophobic, hydrophilic, adhesive, and/or other material(s) to be applied to the substrates, etc.

The example processing system 1000 includes a user interface such as, for example, a graphical user interface (GUI) 1036. An operator or technician interacts with the processing system 1000 and, thus, the example assembly 900 via the interface 1036 to provide, for example, commands related to operation of the rollers 1006*a-n* such as speed, duration of rotation, etc. of the rollers; the pattern(s) to be deposited via the printers 1012*a-n*; materials and patterns of the electrodes, the contacts, the traces, the hydrophilic layers, the hydrophilic channels, the capping layers, and/or the reagents; the size of the discrete units into which the substrates are cut via the dicing station 1032; etc. The interface 1036 may also be used by the operator to obtain information related to the status of any substrate processing completed and/or in progress, check parameters such as speed and alignment, and/or to perform calibrations.

In the example shown, the processing system components 1004, 1008, 1010, 1014, 1018, 1022, 1026, 1030, 1034 are communicatively coupled to other components of the example processing system 1000 via communication links 1038. The communication links 1038 may be any type of wired connection (e.g., a databus, a USB connection, etc.) and/or any type of wireless communication (e.g., radio frequency, infrared, etc.) using any past, present or future communication protocol (e.g., Bluetooth, USB 2.0, USB 3.0, etc.). Also, the components of the example system 1000 may be integrated in one device or distributed over two or more devices.

Figure 11:
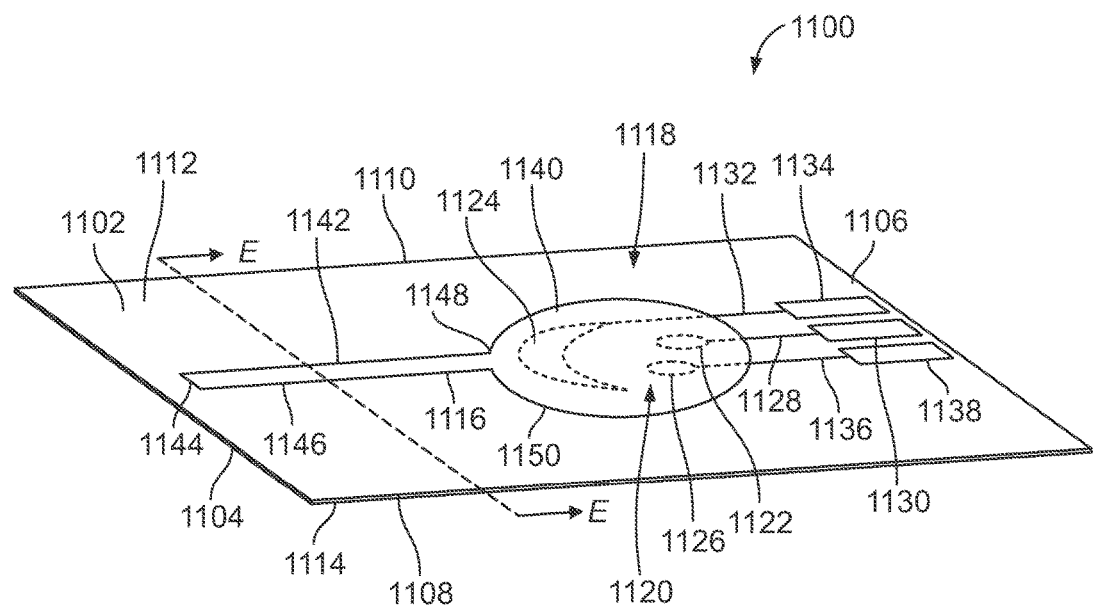
FIG. 11 is a perspective view of another alternative example substrate-based diagnostic device constructed in accordance with the teachings of this disclosure.

FIG. 11 illustrates another example substrate-based diagnostic device 1100 (e.g., a paper-based detection device) that may be used for IA or CC diagnostic testing. Similar to the devices 100 and 700 disclosed above, the device 1100 includes a detection zone, a channel, and/or a capping layer. However, in the device 1100, the detection zone and the channel are defined within an etched channel formed in a top surface of a hydrophobic substrate.

In the illustrated example of FIG. 11, the device 1100 includes a substrate 1102. In the illustrated example, the substrate 1102 is implemented as a piece (e.g., a strip, a sheet, a portion, etc.) of hydrophobic paper. The paper substrate 1102 is fluid impermeable and repels fluids or substantially reduces the amount of fluid that is permeable into the paper substrate 1102. In some examples, the paper substrate 1102 is constructed from hydrophobic material (e.g., from trees and/or chemicals having hydrophobic properties). In other examples, the paper substrate 1102 is standard piece of paper (e.g., having porous and fibers) and has a hydrophobic coating that prevents fluids from permeating into the porous structure of the paper substrate 1102.

In the illustrated example, the paper substrate 1102 has a first end 1104, a second end 1106 opposite the first end 1104, a first side 1108, a second side 1110 opposite the first side 1108, a top surface 1112 and a bottom surface 1114 opposite the top surface 1112. In the illustrated example, the paper substrate 1102 has a substantially rectangular shape. However, in other examples, the paper substrate 1102 may be in another shape such as, for example, a square, a triangle, a circle, an ellipse, an irregular shape, etc.

In the illustrated example, the paper substrate 1102 includes a void or indentation 1116 formed within the top surface 1112 of the paper substrate 1102. The void 1116 defines an area where the channel and detection zone (disclosed in detail below) may be disposed. In this manner, the channel and the detection zone are relatively flush or even with the top surface 1112 of the paper substrate 1102. In some examples, the void 1116 is etched (e.g., via a laser or other suitable means) into the top surface 1112 of the paper substrate 1102.

In the illustrated example, the device 1100 includes a detection zone 1118 (e.g., a test area, a reaction zone, etc.) that defines a location where the test is to occur. The detection zone 1118 has a sensor 1120 for detecting a reaction between the sample and one or more reagents, which is then used to measure the presence, absence and/or concentration of the target analyte in the sample. In the illustrated example, the sensor 1120 includes a first electrode 1122 (e.g., a working electrode), a second electrode 1124 (e.g., a counter-electrode, a ground electrode) and a third electrode 1126 (e.g., a reference electrode). The first, second and third electrodes 1122, 1124, 1126 may operate similar to the first, second and third electrodes 120, 122, 124 of the example device 100 disclosed above. In the illustrated example, however, the first, second, and third electrodes 1122, 1124, 1126 are printed into the void 1116 formed in the top surface 1112 of the paper substrate 1102. Because the paper substrate 1102 is hydrophobic, the conductive ink of the first, second, and third electrodes 1122, 1124, 1126 does not permeate into the material of the substrate 1102. In some examples, the one or more of the electrodes 1122, 1124, 1126 are made of gold (Au), gold on silver chloride (AgCl), carbon (C), and/or silver/silver chloride (Ag/AgCl). The one or more of the electrodes 1122, 1124, 1126 may be printed into the substrate 1102 using, for example, gravure printing, flexographic printing, screen printing, rotary screen printing, and/or inkjet printing. In other examples, other suitable types of printing processes may be employed to print the conductive ink into the paper substrate 1102.

In the illustrated example, the device 1100 includes a first trace 1128 that electrically couples the first electrode 1122 to a first contact 1130, a second trace 1132 that electrically couples the second electrode 1124 to a second contact 1134, and a third trace 1136 that electrically couples the third electrode 1126 to a third contact 1138. The device 1100 may be used by an electric reader (e.g., the reader 400) and the contacts 1130, 1134, 1138 enable the reader to electrically communicate with the electrodes 1122, 1124, 1126 and sense electrical signal including the changes in, for example, amps, volts and/or resistance.

To enable a sample to contact the sensor 1120 during the reaction, the detection zone 1118 of the illustrated example includes a layer of material suspension 1140 (e.g., hydrophilic ink) that is disposed within the void 1116 and over the sensor 1120 and/or the area surrounding the sensor 1120. The layer 1140 facilitates transport of a fluid sample. The material suspension or hydrophilic ink may be similar to the hydrophilic ink disclosed for the layer 138 of the device 100 and may be deposited using printing processed disclosed above.

To transfer or move a fluid sample to the detection zone 1118, the example device 1100 includes a channel 1142 of the material suspension or hydrophilic ink (e.g., silica, porous material). In the illustrated example, the hydrophilic ink is disposed within the void 1116. In this manner, the hydrophilic ink of the channel 1142 wicks the fluid sample via capillary action from one end for the channel 1142 to the other end of the channel 1142. Specifically, in the illustrated example, the channel 1142 includes a sample deposit area or a first end 1144 (e.g., an inlet), a middle section 1146, and a second end 1148 (e.g., an outlet). The second end 1148 is in contact with the layer 140 of hydrophilic ink of the detection zone 1118. The material suspension or hydrophilic ink may be similar to the hydrophilic ink disclosed for the channel 140 of the device 100 and may be deposited using printing processes disclosed above.

Figure 12:
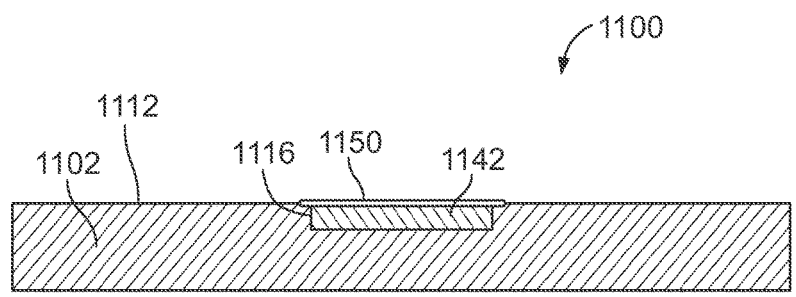
FIG. 12 is a cross-sectional view taken along line E-E in FIG. 11 of the example substrate-based diagnostic device of FIG. 11.

FIG. 12 is a cross-sectional view of the device 1100 taken along line E-E of FIG. 11. In the illustrated example, the void 1116 is formed in the top surface 1112 of the paper substrate 1102. The void 1116 may be in any shape or pattern to define the geometry of the channel and detection zone printed therein. In the illustrated example, the hydrophilic ink of the channel 1142 is printed into the void 1116 such that the top of the channel 1142 is substantially flush or even with the top surface 1112 of the paper substrate 1102. In other examples, the channel 1142 extends above or past the top surface 1112 of the paper substrate 1102.

In some examples, one or more reagents are printed into the void 1116 and/or onto one or more of the electrodes 1122, 1124, 1126 prior to the hydrophilic ink. As the sample wicks through the channel 1142 and into the layer 1140 of the detection zone 1118, the sample interacts with the reagent(s) and the biomolecular interaction can then be detected by the electrodes 1122, 1124, 1126. The reagent(s) may be printed using, for example, in-line inkjet printing or high-throughput printing such as, for example, flexographic printing, screen printing, or slot die deposition. In some examples, the reagent(s) may be embedded in a hydrogel or other polymer(s) and printed as a suspension that is later cured (e.g., via ultra-violet light or electropolymerization). In some examples, a plurality of electrodes is employed to perform different types of assays and the electrodes may be functionalized with different binding reagents to detect a plurality of analytes.

In some examples, a capping layer 1150 is printed on top of the channel 1142 and the detection zone 1118 to prevent the evaporation of sample and/or reduce the risk of contamination. The capping layer 1150 creates a fluid-impermeable (or hydrophobic) surface over the top of the hydrophilic ink of the channel 1142 and the layer 1140 of the detection zone 1118. In some examples, the capping layer 1150 is not disposed on top of the inlet 1144 of the channel 1142, so that the fluid sample may be deposited at the inlet 1144 of the channel 1142. In other examples, the entire channel 1142 is covered with the capping layer 1150 and an opening or hole may be defined in the capping layer to allow the fluid sample to come into contact with the substrate 1102 at the inlet 1144 of the channel 1142.

The example device 1100 illustrated in FIG. 11 may be created using an assembly similar to the example assembly 500 disclosed above. An additional etching step may be included in the assembly to form the void in the substrate prior to the printing process(es).

While an example manner of implementing the assembly 500 and/or the assembly 900 of FIGS. 5 and 9 is illustrated in FIGS. 6 and 10, one or more of the elements, processes and/or devices illustrated in FIGS. 6 and 10 may be combined, divided, re-arranged, omitted, eliminated and/or implemented in any other way. Further, the example controllers 602, 1002, the example roller driver(s) 604, 1004, the example processor 608, 1008, the example printer driver(s) 610, 1010, the example sintering station driver(s) 1014, the example mesh lamination driver(s) 1018, the example laser driver(s) 1022, the example dicing station driver(s) 614, 1030, the example databases 618, 1034 and/or, more generally, the example processing systems 600 and 1000 of FIGS. 6 and 10 may be implemented by hardware, software, firmware and/or any combination of hardware, software and/or firmware. Thus, for example, any of the example controllers 602, 1002, the example roller driver(s) 604, 1004, the example processor 608, 1008, the example printer driver(s) 610, 1010, the example sintering station driver(s) 1014, the example mesh lamination driver(s) 1018, the example laser driver(s) 1022, the example dicing station driver(s) 614, 1030, the example databases 618, 1034 and/or, more generally, the example processing systems 600 and 1000 of FIGS. 6 and 10 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example, controllers 602, 1002, the example roller driver(s) 604, 1004, the example processor 608, 1008, the example printer driver(s) 610, 1010, the example sintering station driver(s) 1014, the example mesh lamination driver(s) 1018, the example laser driver(s) 1022, the example dicing station driver(s) 614, 1030, and/or the example databases 618, 1034 are hereby expressly defined to include a tangible computer readable storage device or storage disk such as a memory, a digital versatile disk (DVD), a compact disk (CD), a Blu-ray disk, etc. storing the software and/or firmware. Further still, the example processing systems 600 and 1000 of FIGS. 6 and 10 may include one or more elements, processes and/or devices in addition to, or instead of, those illustrated in FIGS. 6 and 10 and/or may include more than one of any or all of the illustrated elements, processes and devices.

Figure 13:
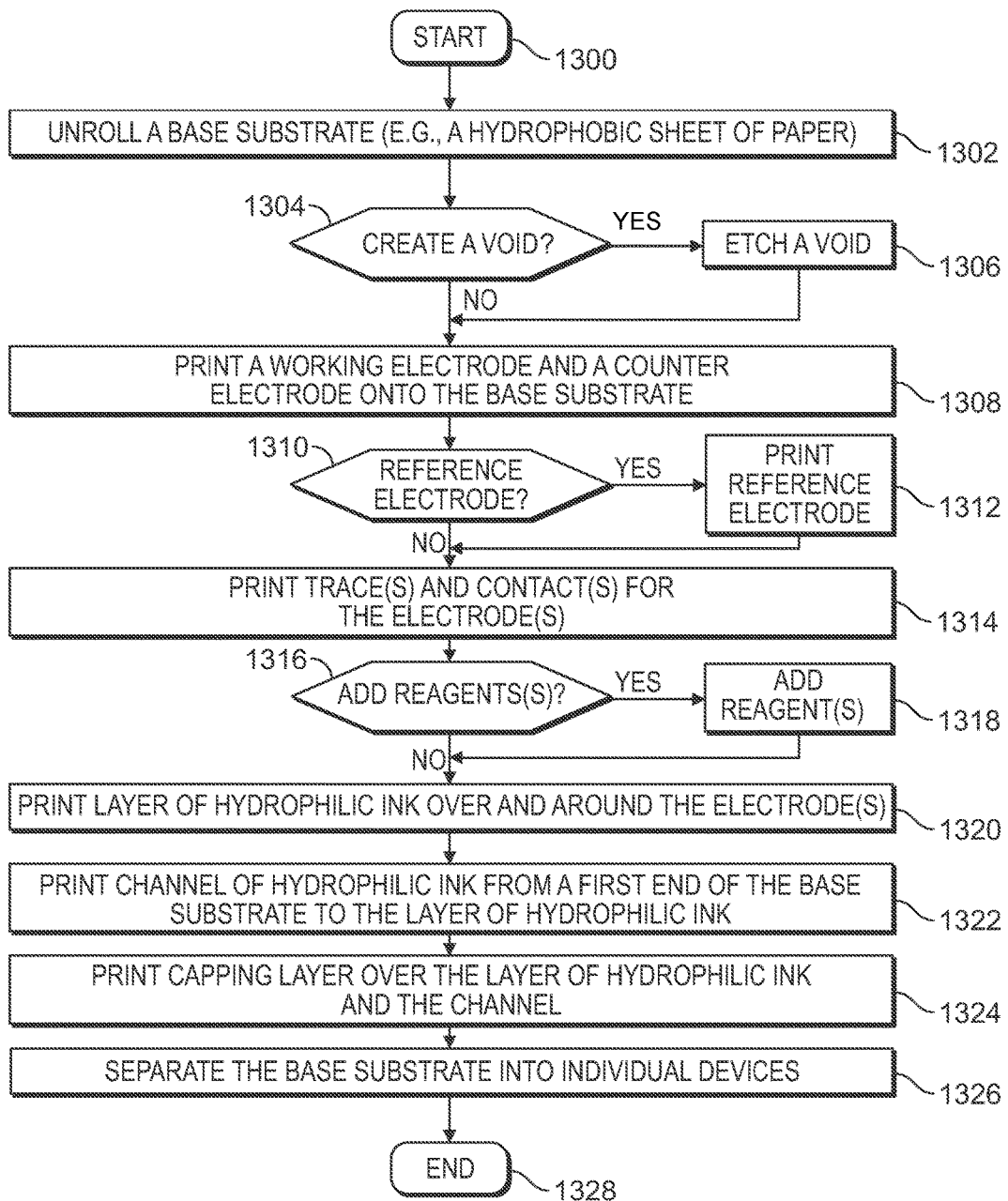
FIG. 13 is a flow diagram of an example method that can be used to implement the example assemblies disclosed herein and construct the example substrate-based diagnostic devices of FIGS. 1 and 11.
Figure 14:
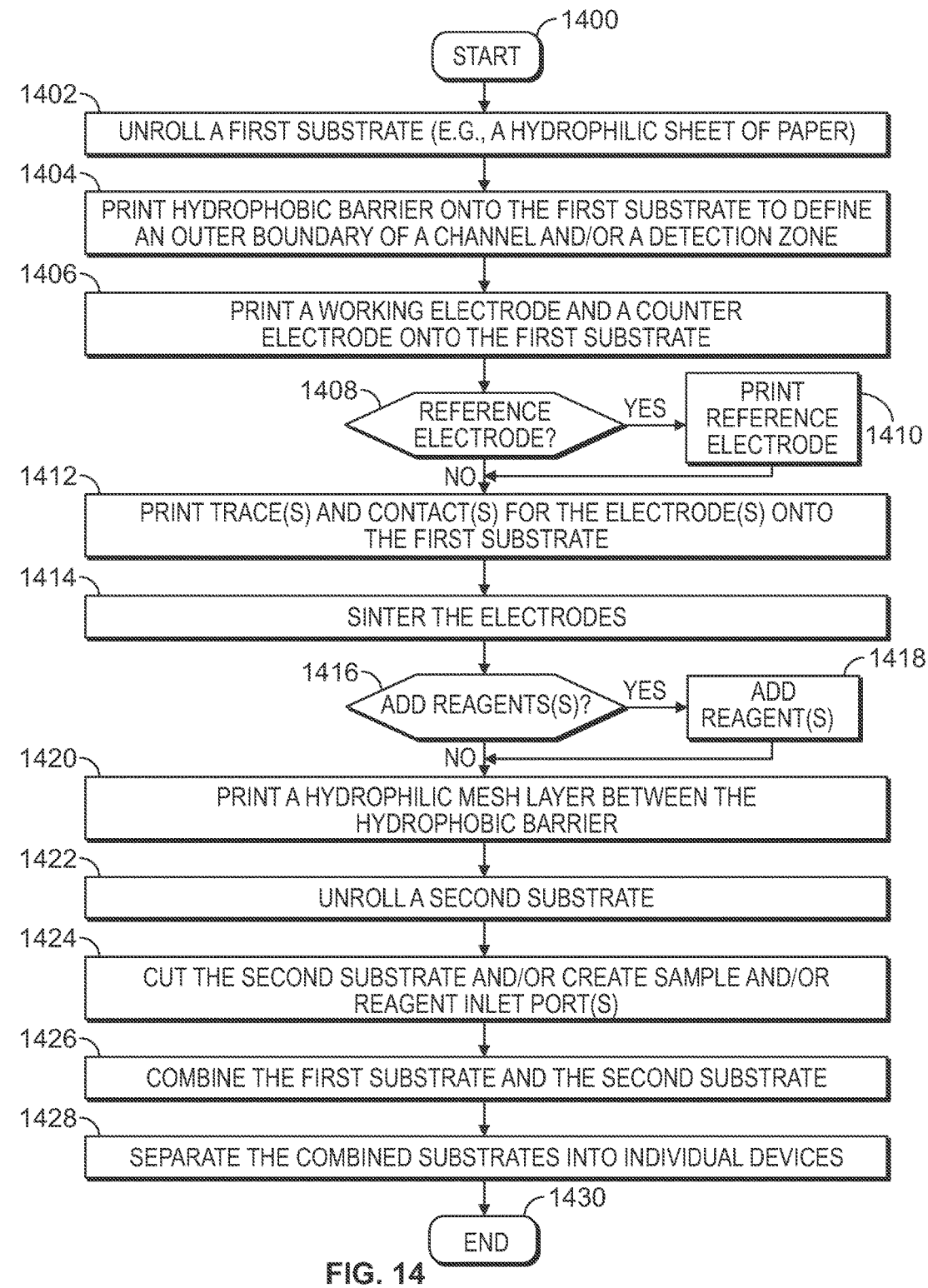
FIG. 14 is a flow diagram of an alternative example method that can be used to implement the example assemblies disclosed herein and construct the example substrate-based diagnostic device of FIG. 7.

Flowcharts representative of example machine readable instructions for implementing the example processing systems 600 and 1000 of FIGS. 6 and 10 are shown in FIGS. 13 and 14. In this example, the machine readable instructions comprise a program for execution by a processor such as the processor 1512 shown in the example processor platform 1500 discussed below in connection with FIG. 15. The program may be embodied in software stored on a tangible computer readable storage medium such as a CD-ROM, a floppy disk, a hard drive, a digital versatile disk (DVD), a Blu-ray disk, or a memory associated with the processor 1512, but the entire program and/or parts thereof could alternatively be executed by a device other than the processor 1512 and/or embodied in firmware or dedicated hardware. Further, although the example program is described with reference to the flowchart illustrated in FIGS. 13 and 14, many other methods of implementing the example processing systems 600 and 1000 of FIGS. 6 and 10 may alternatively be used. For example, the order of execution of the blocks may be changed, and/or some of the blocks described may be changed, eliminated, or combined.

As mentioned above, the example processes of FIGS. 13 and 14 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example processes of FIGS. 13 and 14 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended.

FIG. 13 depicts an example flow diagram representative of an example method 1300 for creating a substrate-based diagnostic device such as, for example, the device 100 and/or the device 1100, using, for example, the assembly 500 illustrated in FIG. 5 and implemented/controlled by the processing system 600 illustrated in FIG. 6. The example method 1300 includes unrolling a base substrate (block 1302). In the illustrated example, the base substrate is a hydrophobic (e.g., fluid impermeable, fluid resistant) sheet of paper (e.g., a continuous sheet of paper). In some examples, the base substrate is manufactured of tree pulp and/or chemicals that result in hydrophobic paper. In other examples, the base substrate may be a traditional sheet of paper that has been coated or treated with a hydrophobic layer or coating (e.g., wax). The hydrophobic sheet of paper may correspond to, for example, the paper substrate 102 of the device 100, the base substrate 506 of the assembly 500 and/or the paper substrate 1102 of the device 1100. The paper substrate 102, the base substrate 506 and/or the paper substrate 1102 provide a support surface for the sensor(s) and hydrophilic ink(s) to be printed onto the substrate. The unrolling of the base substrate may be controlled, for example, by the roller driver(s) 604.

In some examples, the method 1300 includes determining whether a void or indentation is to be created in the surface of the base substrate (block 1304). A void or indentation provides an area where a channel and/or detection zone (disclosed in detail below) may be deposited. The walls of the void assist in forming the shape of the channel and/or detection zone. If a void is to be created in the base substrate, the method 1300 includes etching a void (block 1306). In some examples, the void is etched using a laser. For example, the device 1100 includes the void 1116 that forms or defines an area where the channel 1142 and the detection zone 1118 are disposed.

The example method 1300 includes printing a working electrode and a counter electrode onto the base substrate (block 1308). The working electrode and counter electrode form an electrical sensor that can be used to determine the presence, absence and/or concentration of a target analyte in a sample. Different electrical techniques such as amperometric, voltammetric and/or potentiometric techniques may be implemented. The working electrode and counter electrode may be printed onto the base substrate (e.g., on the top surface of the base substrate or in a void in the top surface of the base substrate) via a rotary screen printer using, for example, conductive (e.g., metallic) inks. For example, in the device 100 of FIG. 1, the first electrode 120 and the second electrode 122 are disposed on the top surface 112 of the paper substrate 102. Similarly, in the device 1100 of FIG. 11, the first electrode 1122 and the second electrode 11224 are disposed within the void 1116 in the paper substrate 1102. In the example processing assembly of FIG. 5, the working and/or counter electrodes are printed onto the base substrate 506 at the first and/or second printing stations 508, 510, which are implemented as rotary screen printers. The electrode printing stations may be controlled by, for example, the printer driver(s) 610 of the processing system 600 illustrated in FIG. 6. In other examples, other types of sensors may be printed onto the base substrate. For example, some devices may include an optical or magnetic sensor, and the components thereof may be deposited onto the base substrate (or within a void in the base substrate).

The example method 1300 includes determining whether a reference electrode is to be utilized (block 1310). In some examples, a reference electrode is used and the difference between the working/counter electrode pair and the reference/counter electrode pair is used in the determining the change across the electrodes. The difference may be correlated with the change affected by the sample and reagent and, thus, is indicative of the presence, absence and/or concentration of the target analyte. If a reference electrode is to be added, the example method 1300 includes printing the reference electrode (block 1312). In some examples, the reference is printed onto the base substrate (or within a void in the base substrate) by a rotary screen printer. For example, in the device 100 of FIG. 1, the third electrode 124 may be a reference electrode. The third electrode 124 is disposed on the top surface 112 of the paper substrate 102. The difference between the first and second electrode 120, 122 pair (e.g., the working/counter electrode pair) can be measured against the second and third electrode 122, 124 pair (e.g., the reference/counter electrode pair). Similarly, in the example device 1100 of FIG. 11, the third electrode 1126 may be a reference electrode. In some examples, the difference between the two pairs of electrodes is indicative of the presence, absence and/or concentration of the target analyte. In the example assembly 500, the first and/or second printing stations 508, 510 are utilized to print the reference electrode onto the base substrate 506. In some examples, the working and counter electrodes may include different material than the reference electrode. In such an instance, one of the first or second printing stations 508, 510 may include a first conductive ink (e.g., Au) for printing the working and counter electrodes and the other of the first or second printing stations 508, 510 may include a second conductive ink (e.g., Ag/AgCl) for the reference electrode. The reference electrode printing may be controlled by, for example, the printer driver(s) 610.

The example method 1300 includes printing a trace and a contact for the each of the electrodes (block 1314). In some examples, a trace (e.g., a wire or a lead) is printed onto the base substrate (or within a void in the base substrate) between one of the electrodes and a corresponding contact. The contacts are utilized to electrically couple the electrodes (which may be covered with hydrophilic ink and a capping layer) to a reader that can sense electrical signals including, for example, signals indicative of change(s) in volts, amps, and/or resistance across the electrodes. In some examples, the contacts of the electrodes are disposed near a similar edge of the base substrate, and so that the edge may be utilized with the read that can easily contact all contacts at the same time. For example, the device 100 of FIG. 1 includes the traces 126, 130, 134 and the contacts 128, 132, 136 for the respective electrodes 120, 122, 124. The traces 126, 130, 134 and the contacts 128, 132, 136 are disposed on the top surface 112 of the paper substrate 102. In the illustrated example of FIG. 1, the contacts 128, 132, 136 are all disposed along the second end 106 of the paper substrate 102. As illustrated in FIG. 4, the second end 106 can then be inserted into the reader 400. Similarly, in the example device 1100 includes traces 1128, 1132, 1136 and contacts 1130, 1134, 1138 for the respective first, second, and third electrodes 1122, 1124, 1126. In the example assembly 500, the first and/or second printing stations 508, 510 may be utilized to print the trace(s) and the contact(s) onto the base substrate 506 (or within a void in the base substrate 506). In some examples, the trace(s) and the contact(s) are printed during the same printing step as the electrodes. In other examples, they are printed on separately. The trace(s) and contact(s) printing may be controlled by, for example, the printer driver(s) 610.

The example method 1300 includes determining whether one or more reagents are to be included with the device (block 1316). For example, with IA and CC testing, one or more reagents are typically used to react with the sample. If a reagent is to be used, the example method 1300 includes adding the reagent (block 1318). In some examples, one or more reagents may be printed onto the working electrode as a reagent ink. Additionally or alternatively, one or more reagents may be printed around the electrodes and/or along the area where the channel of hydrophilic ink is to be printed. For example, in the example device 100 of FIGS. 1 and 2A-2F, the reagent 200 is printed onto the top of the first electrode 120. As the sample contacts the first electrode 120 the sample interacts with the reagent. In the example assembly 500 of FIG. 5, a reagent is printed onto the base substrate 506 at the third printing station 512. In some examples, the third printing station 512 is implemented as an inkjet printer.

The addition of reagent(s) may be controlled by, for example, the printer driver(s) 610.

The example method 1300 includes printing a layer of suspension material or hydrophilic ink over and around the electrodes (block 1320). The layer of hydrophobic ink on top of the electrodes forms a detection zone, where the sample can wet the electrodes and, thus, the electrodes can sense the biomolecular interaction occurring. In some examples, the hydrophilic ink includes particles (e.g., micro-beads or nano-beads) that cause the sample to wick through the material of the ink and, thus, spread around the electrodes. For example, in the example device 100 of FIG. 1, the detection zone 116 includes the layer of hydrophobic ink 138, which is disposed over and around the electrodes 120, 122, 124 on the top surface 112 of the paper substrate 102. The layer 138 wicks (e.g., via capillary action) a fluid sample through the layer so the sample comes into contact with the reagent and the electrodes 120, 122, 124. Similarly, in the example device 1100, the layer 1140 is deposited into the void 1116 over the electrodes 1122, 1124, 1126 to form the detection zone 1116. In the example assembly 500 of FIG. 5, the layer of hydrophilic ink may be printed onto the base substrate 506 (or within a void in the base substrate) by at the fourth printing station 514. In the illustrated example, the fourth printing station 514 is implemented as a rotary screen printer. The hydrophilic ink layer printing may be controlled, for example, by the printer driver(s) 610.

The example method 1300 includes printing a channel of suspension material or hydrophilic ink from a first end of the base substrate (or at positions on a roll of substrate that will become an end once the roll is cut into separate devices) to the layer of the hydrophilic ink (block 1322). The channel provides a pathway for the sample to be transferred to the layer of hydrophilic ink at the detection zone. In some examples, the channel is formed by a substantially straight path leading from a first end of the base substrate to the layer. Other examples include multiple channels, branched channels, and/or channels with one or more curved portion(s). A sample deposited onto/into the channel will be transported to the layer and, thus, onto the electrodes. For example, the device 100 of FIG. 1 includes the channel 140, which has the first end 142 and the second end 146 that connects with the layer 138. Similarly, in the example device 1100, the channel 1142 is deposited into the void 1116 to form the channel 1140. In the example assembly 500 of FIG. 5, the channel of hydrophilic ink may be printed onto the base substrate by the fourth printing station 514. In some examples, the ink of the channel and the layer are the same, and the channel and the layer may be printed onto the base substrate 506 at the same time using the rotary screen printer. The channel printing may be controlled by, for example, the printer driver(s) 610.

The example method 1300 includes printing a capping layer over the layer of hydrophilic ink and the channel (block 1324). The capping layer is a fluid impermeable or hydrophobic layer that reduces evaporation of sample and/or the risk of contamination. In some examples, the capping layer is printed over the top and sides of the hydrophilic layer and the hydrophilic channel to define a fluid-tight pathway created by the capping layer (e.g., the upper boundary) and the base substrate (e.g., the bottom layer), with the layer and the channel therebetween. For example, the device 100 of FIG. 1 includes the capping layer 148. FIGS. 2F, 3A, and 3B illustrate the arrangement of the capping layer 148 over the layer 138 and the channel 140. In the example device 1100, the channel 1142 and the detection zone 1118 are formed within the void 1116 in the substrate 1102. In such an example, the capping layer 1150 may be printed over the channel 1142 and the detection zone 1118 to form the hydrophilic channel between the capping layer and the surfaces of the void 1116. In the example assembly 500 of FIG. 5, for example, the capping layer may be printed onto the base substrate 506 by the fifth printing station 516. In some examples, the fifth printing station 516 is implemented by a rotary screen printer. The capping layer printing may be controlled by, for example, the printer driver(s) 610.

The example method 1300 includes separating the base substrate into individual devices (block 1326). In some examples, the method is implemented via a R2R or web-based manufacturing process. Multiple devices may be printed onto the continuous base substrate. The base substrate may be cut or diced into the individual devices. In the example assembly 500 of FIG. 5, the optional dicing station 518 is employed to cut or serrate the base substrate 506 into the individual devices. The separation or dicing may be controlled by, for example, the dicing station driver(s) 614.

At the end of the example method 1300 (block 1328) the individual device can be used to perform, for example, IA or CC testing on the base substrate. The resulting device is a relatively cheap and disposable diagnostic device that can provide fast and reliable results in a POC setting.

FIG. 14 depicts an example flow diagram representative of an alternative example method 1400 for creating a substrate-based diagnostic device such as, for example, the device 700, using, for example, the assembly 900 illustrated in FIG. 9. The example method 1400 includes unrolling a first substrate (block 1402). The first substrate acts as a support for building the diagnostic device. In the illustrated example, the first substrate is a hydrophilic sheet of paper (e.g., a continuous sheet of paper). The hydrophilic sheet of paper absorbs liquids such as, for example, inks. The hydrophilic substrate may correspond to, for example, the paper substrate 702 of the device 700 and/or the base substrate 906 in the example assembly 900. The unrolling of the first substrate may be controlled, for example, by the roller driver(s) 1004.

The example method 1400 includes printing a hydrophobic barrier onto the first substrate to define an outer boundary of a channel and/or a detection zone (block 1404). The hydrophobic barrier is printed using a hydrophobic ink. The hydrophobic ink may be printed onto the first substrate in a pattern that defines the outer boundary of a channel and/or a detection zone (disclosed herein). The hydrophobic ink absorbs into the material of the first substrate and, as a result, create a pathway or channel where fluid may be wicked through the first substrate. For example, in the device 700 of FIG. 7, the hydrophobic barrier 738 is a line of hydrophobic ink that is disposed in the substrate 702. The example barrier 738 defines the outer boundary of the channel 742 and the detection zone 718 and prevents a fluid sample from wicking into areas of the substrate 702 outside of the barrier 738. In the example assembly 900, a hydrophobic ink is printed onto the substrate 906 at the first printing station 908. The barrier printing may be controlled by, for example, the printer driver(s) 1010.

In the example method 1400, a working electrode and a counter electrode onto the first substrate (block 1406). The working electrode and counter electrode form an electrical sensor that can be used to determine the presence, absence and/or concentration of a target analyte in a sample. Different electrical techniques such as amperometric, voltammetric and/or potentiometric techniques may be implemented. The working electrode and counter electrode may be printed onto the first substrate using, for example, conductive (e.g., metallic) inks. The conductive inks absorb into the first substrate and form metallic electrodes within the material of the first substrate. For example, in the device 700 of FIG. 7, the first electrode 720 and the second electrode 722 are printed into the paper substrate 702. In the example processing assembly of FIG. 9, the working and/or counter electrodes are printed onto the substrate 906 at the third printing station 912, which is implemented an inkjet printer. The inkjet printer may print AuNP ink that is used to form the working and counter electrodes. The electrode printing may be controlled by, for example, the printer driver(s) 1010. In other examples, other types of sensors may be printed onto the first substrate. For example, some devices may include an optical or magnetic sensor, and the components thereof may be deposited onto the first substrate (or within a void in the first substrate).

The example method 1400 includes determining whether a reference electrode is to be utilized (block 1408). In some examples, a reference electrode is used and the difference between the working/counter electrode pair and the reference/counter electrode pair is used in the determining the change across the electrodes. The difference may be correlated with the change affected by the sample and reagent and, thus, is indicative of the presence, absence and/or concentration of the target analyte. If a reference electrode is to be added, the example method 1400 includes printing the reference electrode (block 1410). For example, in the device 700 of FIG. 7, the third electrode 724 may be a reference electrode. The third electrode 724 is disposed printed onto the paper substrate 702 and is absorbed into the material of the paper substrate 702. In the example assembly 900, the second printing station 910 is utilized to print the reference electrode onto the base substrate 906. In the illustrated example of FIG. 9, the second printing station 910 is implemented as a rotary screen printer and includes a conductive ink such as, for example, Ag/AgCl. The reference electrode printing may be controlled by, for example, the printer driver(s) 1010.

The example method 1400 includes printing a trace and a contact for the each of the electrodes onto the first substrate (block 1412). In some examples, a trace (e.g., a wire or a lead) is printed onto the first substrate between one of the electrodes and a corresponding contact. The contacts are utilized to electrically couple the electrodes (which may be disposed within the material of the first substrate) to a reader that can sense electrical signals including, for example, signals indicative of change(s) in volts, amps, and/or resistance across the electrodes. In some examples, the contacts of the electrodes are disposed near a similar edge of the first substrate, and so that the edge may be utilized with the reader that can easily contact all contacts at the same time. For example, the device 700 of FIG. 7 includes the traces 726, 730, 734 and the contacts 728, 732, 736 for the respective electrodes 720, 722, 724. The traces 726, 730, 734 and the contacts 728, 732, 736 are printed using onto the substrate 702 via conductive inks, and the conductive inks absorb into the material of the substrate 702 to define the traces and the contacts. In the example assembly 900, the second and/or third printing stations 910, 912 may be utilized to print the trace(s) and the contact(s) onto the base substrate 906. In some examples, the trace(s) and the contact(s) are printed during the same printing step as the electrodes. In other examples, they are printed on separately. The trace(s) and contact(s) printing may be controlled by, for example, the printer driver(s) 1010.

The example method 1400 includes sintering the electrodes (block 1414). In some examples, pressure and/or heat is applied to one or more of the electrodes to fuse the atoms and molecules of conductive ink to form a solid material in the first substrate. For example, the assembly 900 includes the sintering station 914 that is capable of sintering the electrodes printed onto the substrate 906. The sintering station 914 may operate by applying alternative current or direct current to the electrode material. The sintering may be controlled by, for example, the sintering station driver(s) 1014.

The example method 1400 includes determining whether one or more reagent(s) are to be included with the device (block 1416). For example, with IA and CC testing, one or more reagent(s) are typically used to react with the sample. If a reagent is to be used, the example method 1300 includes adding the reagent (block 1418). In some examples, one or more reagent(s) may be printed onto the working electrode using a reagent ink. Additionally or alternatively, one or more reagent(s) may be printed around the electrodes and/or along the area where the channel of hydrophilic ink is to be printed. In the example assembly 900 of FIG. 9, a reagent is printed onto the substrate 906 at the fourth printing station 916, which is implemented as an inkjet printer. The addition of reagent(s) may be controlled by, for example, the printer driver(s) 1010.

The example method 1400 includes printing a hydrophilic mesh layer between the hydrophobic barrier (block 1420). The hydrophilic mesh layer assists in wicking a fluid sample through the material of the first substrate. The hydrophilic mesh layer may be printed onto the first substrate using a material suspension or hydrophilic ink that includes particles (e.g., micro-beads or nano-beads) that cause the sample to wick through the material of the ink. The hydrophilic mesh layer may define the channel and detection zone of the device. For example, in the example device 700 of FIG. 7, the hydrophilic mesh is disposed between the hydrophobic barrier 738 and defines a pathway for a fluid sample to wick through the channel 742 to the layer 740 of the detection zone. In the example assembly 900 of FIG. 9, the hydrophilic mesh layer is printed onto the base substrate 906 by the mesh lamination unit 918. The mesh printing may be controlled, for example, by the mesh lamination driver(s) 1018.

The example method 1400 includes unrolling a second substrate (block 1422). In this example, the second substrate comprises a hydrophobic material, as disclosed above. In some examples, the second substrate is to be coupled to one side (e.g. the top) of the first substrate and forms a capping layer or fluid impermeable layer over at least the channel and detection zone of the device. For example, in the example device 700 of FIG. 7, the capping layer 746 is disposed over at least the detection zone 716. In the example assembly 900 of FIG. 9, the hydrophobic substrate 922 is unrolled from the third roller 920. The unrolling of the second substrate may be controlled by, for example, the roller driver(s) 1004.

The example method 1400 includes cutting the second substrate and/or creating sample and/or reagent inlet ports in the second substrate (block 1424). In some examples, the second substrate is cut into a shape that substantially matches the shape of the channel and/or the detection zone, so that when the second substrate is coupled to the top of the first substrate, a fluid impermeable seal is created between the second substrate and the hydrophobic barriers in the first substrate. In some examples, a laser is utilized to cut the second substrate. Additionally or alternatively, the laser may be used to change the hydrophobicity of the second substrate to create sample and/or reagent inlet ports. In the example assembly 900 of FIG. 9, the laser 924 is included to cut and/or create inlet ports for the sample and/or reagent. The laser can change the hydrophobicity of the hydrophobic substrate 922, so that a sample and/or a reagent can be passed through the hydrophobic substrate to reach the channel and/or the detection zone in the device. The second substrate cutting may be controlled by, for example, the laser driver(s) 1022.

The example method 1400 also includes combining the first substrate and the second substrate (block 1426). The second substrate may be disposed on top of the first substrate to seal the top of the first substrate. The second substrate assists in prevent evaporation of sample and/or reducing the risk of contamination. In the example assembly 900 of FIG. 9, the lamination unit 926 combines the hydrophobic substrate 922 and the substrate 906. In some examples, the lamination unit 926 utilizes heat and/or pressure to couple the hydrophobic substrate 922 to the top of the substrate 906. The combination of the first substrate and the second substrate may be controlled by, for example, the lamination unit driver(s) 1026.

The example method 1400 includes separating the combined substrates into individual devices (block 1428). In some examples, the method is implemented via a R2R or web-based manufacturing process. Multiple devices may be printed onto the continuous first and second substrates. The combined substrate may be cut or diced into the individual devices. In the example assembly 900 of FIG. 9, the dicing station 928 is employed to cut or serrate the substrate 906 into the individual devices. The separation of the combined substrates into individual device may be controlled by, for example, the dicing station driver(s) 1030.

At the end of the example method 1400 (block 1430) the individual devices can be used to perform, for example, IA or CC testing on the first substrate. The resulting device is a relatively cheap, consumable, disposable diagnostic device that can provide fast and reliable results in a POC setting.

Figure 15:
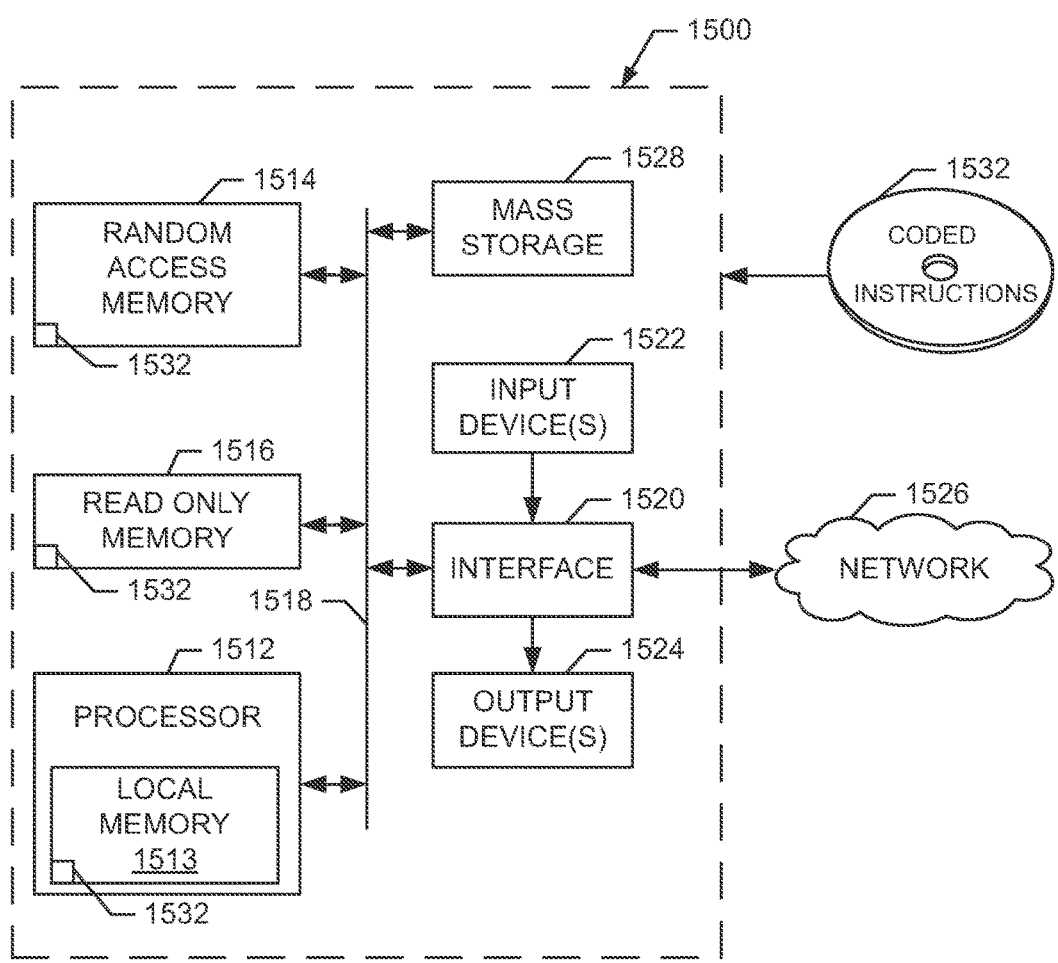
FIG. 15 is an example processor platform that may be used to implement the example methods, systems and/or apparatus disclosed herein.

FIG. 15 is a block diagram of an example processor platform 1500 capable of executing the instructions of FIGS. 13 and 14 to implement the example assembly 500, the example processing system 600, the example assembly 900, and/or the example processing system 1000 of FIGS. 5, 6, 9 and 10. The processor platform 1500 can be, for example, a server, a personal computer, a mobile device (e.g., a cell phone, a smart phone, a tablet such as an iPad™), a personal digital assistant (PDA), an Internet appliance, a DVD player, a CD player, a digital video recorder, a Blu-ray player, a gaming console, a personal video recorder, a set top box, or any other type of computing device.

The processor platform 1500 of the illustrated example includes a processor 1512. The processor 1512 of the illustrated example is hardware. For example, the processor 1512 can be implemented by one or more integrated circuits, logic circuits, microprocessors or controllers from any desired family or manufacturer.

The processor 1512 of the illustrated example includes a local memory 1513 (e.g., a cache). The processor 1512 of the illustrated example is in communication with a main memory including a volatile memory 1514 and a non-volatile memory 1516 via a bus 1518. The volatile memory 1514 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1516 may be implemented by flash memory and/or any other desired type of memory device. Access to the main memory 1514, 1516 is controlled by a memory controller.

The processor platform 1500 of the illustrated example also includes an interface circuit 1520. The interface circuit 1520 may be implemented by any type of interface standard, such as an Ethernet interface, a universal serial bus (USB), and/or a PCI express interface.

In the illustrated example, one or more input devices 1522 are connected to the interface circuit 1520. The input device(s) 1522 permit(s) a user to enter data and commands into the processor 1512. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 1524 are also connected to the interface circuit 1520 of the illustrated example. The output devices 1524 can be implemented, for example, by display devices (e.g., a light emitting diode (LED), an organic light emitting diode (OLED), a liquid crystal display, a cathode ray tube display (CRT), a touchscreen, a tactile output device, a printer and/or speakers). The interface circuit 1520 of the illustrated example, thus, typically includes a graphics driver card, a graphics driver chip or a graphics driver processor.

The interface circuit 1520 of the illustrated example also includes a communication device such as a transmitter, a receiver, a transceiver, a modem and/or network interface card to facilitate exchange of data with external machines (e.g., computing devices of any kind) via a network 1526 (e.g., an Ethernet connection, a digital subscriber line (DSL), a telephone line, coaxial cable, a cellular telephone system, etc.).

The processor platform 1500 of the illustrated example also includes one or more mass storage devices 1528 for storing software and/or data. Examples of such mass storage devices 1528 include floppy disk drives, hard drive disks, compact disk drives, Blu-ray disk drives, RAID systems, and digital versatile disk (DVD) drives.

The coded instructions 1532 of FIG. 15 may be stored in the mass storage device 1528, in the volatile memory 1514, in the non-volatile memory 1516, and/or on a removable tangible computer readable storage medium such as a CD or DVD.

From the foregoing, it will appreciated that the above disclosed apparatus, systems and methods provide a reliable, easily fabricated, less expensive disposable diagnostic devices. It is advantageous to use the above-disclosed paper substrate(s) because paper is a readily available material, inexpensive, thin and light weight (e.g., around 10 mg/cm2); is easy store and/or transport; has many properties (e.g., the ability to control hydrophobicity and surface characteristics); is flexible and compatible with many printing methods; is chemically modifiable to immobilize biomolecules; and is compatible with colorimetric assays or electrochemical assays using printed electronics. Additionally, it is advantageous to use the above-disclosed hydrophobic or fluid-impermeable paper substrate(s) because the paper may be formed using any substance that does not interface with the biological reactions but is impermeable to aqueous fluids; the micro-fluidic components and the detection components may be deposited in a continuous web-fed processing using printing technologies; in some examples the process is additive, which reduces material consumption and device cost; sealing the microfluidic channel(s) increase the speed at which the fluid flows through the microfluidic channels and, thus, the device; and the addition of the capping layer forms a defined volume of space to aid in fluid metering.

Although certain example methods, apparatus, systems and articles of manufacture have been disclosed herein, the scope of coverage of this patent is not limited thereto. On the contrary, this patent covers all methods, apparatus, systems and articles of manufacture fairly falling within the scope of the claims of this patent.

What is claimed is:

1. A method of manufacturing a substrate-based diagnostic device, the method comprising:
   depositing a sensor on a top surface of a hydrophobic substrate, the hydrophobic substrate having a first end and a second end opposite the first end;
   depositing a layer of reagent on or around the sensor;
   depositing a layer of hydrophilic ink over the sensor and the layer of reagent, the layer of hydrophilic ink, the sensor, and the layer of reagent forming a detection zone; and
   depositing a pathway of hydrophilic ink onto the top surface of the hydrophobic substrate, the pathway leading from an area adjacent the first end of the hydrophobic substrate to the layer of hydrophilic ink.

2. The method of claim 1, wherein the sensor includes a first electrode and a second electrode.

3. The method of claim 2, wherein depositing the layer of reagent includes depositing the layer of reagent on a top surface of the first electrode.

4. The method of claim 2, wherein depositing the sensor includes printing the first electrode and the second electrode onto the top surface of the hydrophobic substrate.

5. The method of claim 4, further including using a first printer to print the first electrode and using a second printer to print the second electrode.

6. The method of claim 5, further including using a first metallic material to print the first electrode and using a second metallic material, different than the first metallic material, to print the second electrode.

7. The method of claim 5, wherein the first and second printers are screen printers.

8. The method of claim 5, further including printing, using the first and second printers, traces and contacts for the first and second electrodes, respectively, leading from the first and second electrodes to the second end of the hydrophobic substrate.

9. The method of claim 2, wherein the second electrode is disposed closer to the first end of the hydrophobic substrate than the first electrode, the second electrode being a ground electrode.

10. The method of claim 1, wherein depositing the layer of reagent includes printing, via an inkjet printer, the layer of reagent.

11. The method of claim 1, wherein depositing the layer of hydrophilic ink and depositing the pathway of hydrophilic ink include printing the hydrophilic ink using at least one of a flexographic printer, a screen printer, a stencil printer, or an inkjet printer.

12. The method of claim 1, wherein the hydrophilic ink includes micro-beads or nano-beads and a binder to adhere the micro-beads or the nano-beads to the top surface of the hydrophobic substrate.

13. The method of claim 12, wherein the binder includes at least one of polyvinyl chloride (PVC), polyvinylpyrrolidone (PVP), or nanofiber cellulose (NFC).

14. The method of claim 1, further including:
   unrolling a base substrate from a roller, the hydrophobic substrate forming a portion of the base substrate; and
   after depositing the sensor, the layer of reagent, the layer of hydrophilic ink, and the pathway of hydrophilic ink, cutting the portion of the base substrate to separate the substrate-based diagnostic device from a remainder of the base substrate.

15. The method of claim 14, wherein the substrate-based diagnostic device is a first substrate-based diagnostic device, further including:
   forming a second substrate-based diagnostic device from the base substrate adjacent to the first substrate-based diagnostic device by:
      depositing a second sensor on a second top surface of a second hydrophobic substrate, the second hydrophobic substrate forming a second portion of the base substrate;
      depositing a second layer of reagent on or around the second sensor;
      depositing a second layer of hydrophilic ink over the second sensor and the second layer of reagent, the second layer of hydrophilic ink, the second sensor, and the second layer of reagent forming a second detection zone; and
      depositing a second pathway of hydrophilic ink onto the second top surface of the second hydrophobic substrate, the second pathway leading from an area adjacent a first end of the second hydrophobic substrate to the second layer of hydrophilic ink; and
   cutting the second portion of the base substrate to separate the second substrate-based diagnostic device from the remainder of the base substrate.

16. The method of claim 1, further including, prior to depositing the sensor, the layer of reagent, the layer of hydrophilic ink, and the pathway of hydrophilic ink, forming an indentation in the top surface of the hydrophobic substrate.

17. The method of claim 16, wherein the sensor, the layer of hydrophilic ink and the pathway of hydrophilic ink are deposited into the indentation.

18. The method of claim 17, wherein a top of the layer of hydrophilic ink and the pathway of hydrophilic ink are substantially even with the top surface of the hydrophobic substrate around the indentation.

19. The method of claim 16, wherein forming the indentation includes etching, with a laser, the indentation in the top surface of the hydrophobic substrate.

* * * * *